(12) United States Patent
Swan et al.

(10) Patent No.: US 6,545,752 B1
(45) Date of Patent: Apr. 8, 2003

(54) METHOD AND APPARATUS FOR DETECTING DEFECTS ALONG THE EDGE OF ELECTRONIC MEDIA

(75) Inventors: Alan J. Swan, Keiser, OR (US); Thomas J. Hafner, Beaverton, OR (US); John Howells, Redmond, OR (US)

(73) Assignee: Daitron, Inc., Wilsonville, OR (US)

(*) Notice: Subject to any disclaimer, the term of this patent is extended or adjusted under 35 U.S.C. 154(b) by 0 days.

(21) Appl. No.: 09/895,899

(22) Filed: Jun. 29, 2001

Related U.S. Application Data

(60) Provisional application No. 60/217,063, filed on Jul. 10, 2000, and provisional application No. 60/216,597, filed on Jul. 7, 2000.

(51) Int. Cl.⁷ .......................... G01N 21/00; G01R 31/26
(52) U.S. Cl. ................ 356/237.4; 356/237.1; 356/237.5; 438/16
(58) Field of Search ............ 356/237.1–237.6, 356/601, 614, 71, 239.1, 239.5, 293.7, 239.8; 438/16, 928; 324/537

(56) References Cited

U.S. PATENT DOCUMENTS

| | | | |
|---|---|---|---|
| 3,988,068 A | * 10/1976 | Sprague | 356/239 |
| 4,213,042 A | 7/1980 | Beach et al. | |
| 5,072,128 A | * 12/1991 | Hayano et al. | 356/237.1 |
| 5,114,230 A | * 5/1992 | Pryor | 356/614 |
| 5,504,345 A | 4/1996 | Bartunek et al. | |
| 5,592,295 A | 1/1997 | Stanton et al. | |
| 5,706,081 A | 1/1998 | Fukasawa et al. | |
| 5,798,831 A | 8/1998 | Hagiwara | |
| 5,898,492 A | 4/1999 | Imaino et al. | |
| 5,903,342 A | 5/1999 | Yatsugake et al. | |
| 5,936,726 A | * 8/1999 | Takeda et al. | 356/237.2 |
| 6,038,019 A | 3/2000 | Chang et al. | |
| 6,062,084 A | 5/2000 | Chang et al. | |
| 6,656,580 | * 12/2000 | Wooten et al. | 438/16 |
| 6,172,745 B1 | * 1/2001 | Voser et al. | 356/71 |

FOREIGN PATENT DOCUMENTS

JP 08-104202 3/1996

* cited by examiner

Primary Examiner—Frank G. Font
Assistant Examiner—Sang H. Nguyen
(74) Attorney, Agent, or Firm—Klarquist Sparkman LLP

(57) ABSTRACT

An electronic media edge defect detector in one form has plural light sources and detectors arranged to direct and receive deflected light from the side edge margins and outer edge margins of the electronic media. The detected light is analyzed to detect the presence of defects. Individual wafers may be raised while in a cassette and turned during the inspection without removing the wafers from the cassette.

23 Claims, 20 Drawing Sheets

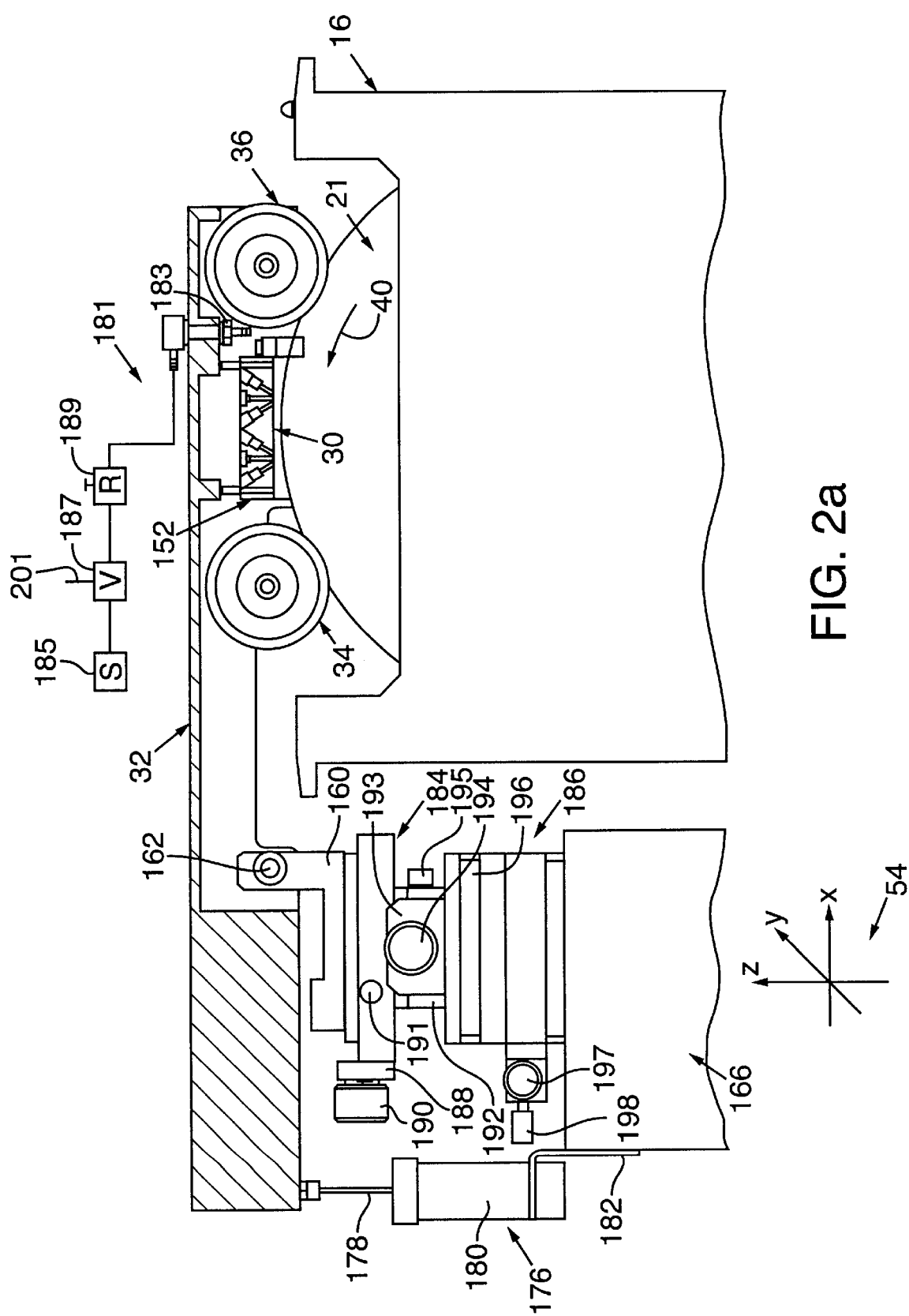

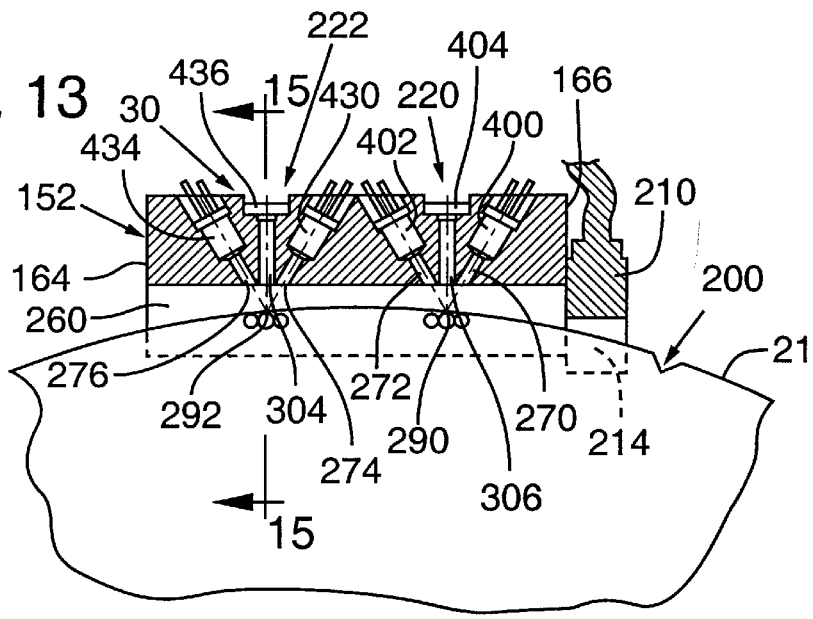
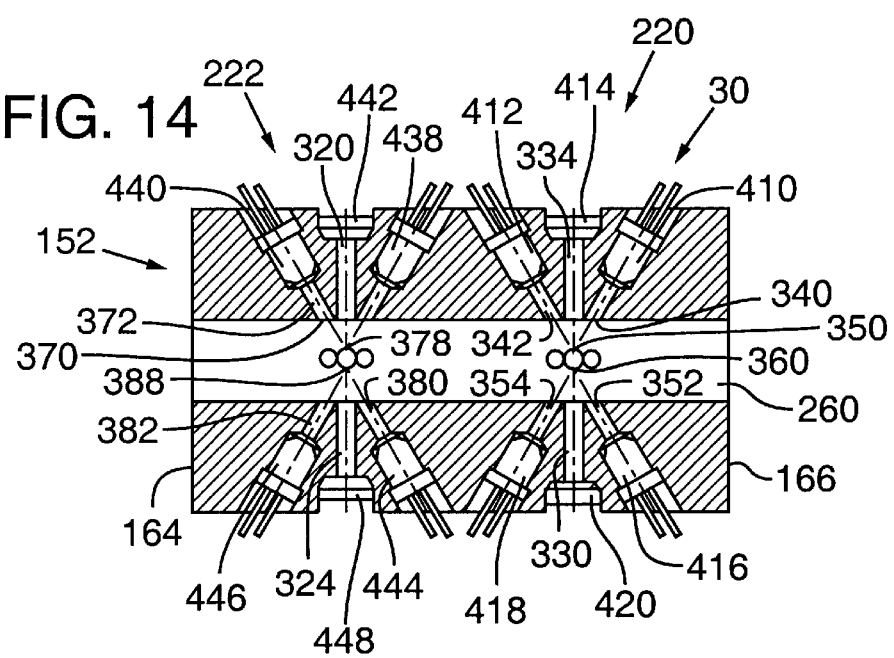
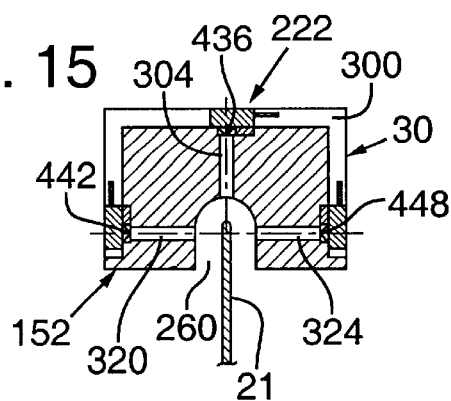

METHOD AND APPARATUS FOR DETECTING DEFECTS ALONG THE EDGE OF ELECTRONIC MEDIA

CROSS REFERENCE

This application is based on Provisional Patent Application No. 60/216,597, filed on Jul. 7, 2000, entitled, "Method And Apparatus For Detecting Defects Along The Edge Of Electronic Media", by John Howells, Alan J. Swan and Thomas J. Hafner, and Provisional Patent Application No. 60/217,063, filed on Jul. 10, 2000, entitled, "Method And Apparatus For Detecting Defects Along The Edge Of Electronic Media", by John Howells, Alan J. Swan and Thomas J. Hafner. The entire disclosures of the above mentioned provisional applications are hereby incorporated in their entirety by reference herein.

SUMMARY

The present invention relates to a method and apparatus for, among other aspects, inspecting and determining the presence of defects along the edge of electronic media. For purposes of this description, the term "electronic media" refers to data storage media such as hard disks, DVDs, CD ROMs and the like, and also encompasses other media which contains or is to contain circuits and/or electronic information or data, such as semi-conductor wafers. The media may assume a variety of shapes although a specific embodiment described below has particularly applicability to electronic media in disk form.

Electronic media such as semi-conductor wafers in disk form may contain defects at the outer edge and along both side edge margins of the wafer. These defects can take various forms such as chips, cracks, scratches and marks on the surfaces near the edge of the wafer.

By determining the presence of defects, decisions can be made whether to discard the electronic media or process it in a way that avoids the defect containing portion of the media.

A need exists for an improved method and apparatus for detecting defects along the edge and edge margins of electronic media such as electronic information storage and/or circuit containing disks. The present invention is directed toward new and unobvious acts, steps and features as described below, both alone and in combination with one another. Thus, the invention is not limited to a method or apparatus which contains all of the features or addresses all of the advantages described below in connection with various embodiments of the invention.

BRIEF DESCRIPTION OF THE DRAWINGS

FIG. 2a is a partially broken away vertical sectional view through a portion of an apparatus, similar to FIG. 2, to illustrate an alternative specific form of such an apparatus.

FIG. 13 is a view like FIG. 11 shown with LEDs and detectors in place, together with a wafer notch detector, and also illustrating a portion of a semi-conductor wafer (shown in transparent form for convenience, it being understood that these wafers are typically optically reflective).

FIG. 14 is a view like FIG. 10 with the LEDs and light detectors shown in place.

FIG. 15 is a view like FIG. 12 with light detectors in place and also showing portions of the outer edge and side edge margins of a wafer toward which the detectors are focused.

DETAILED DESCRIPTION

Figure 1:
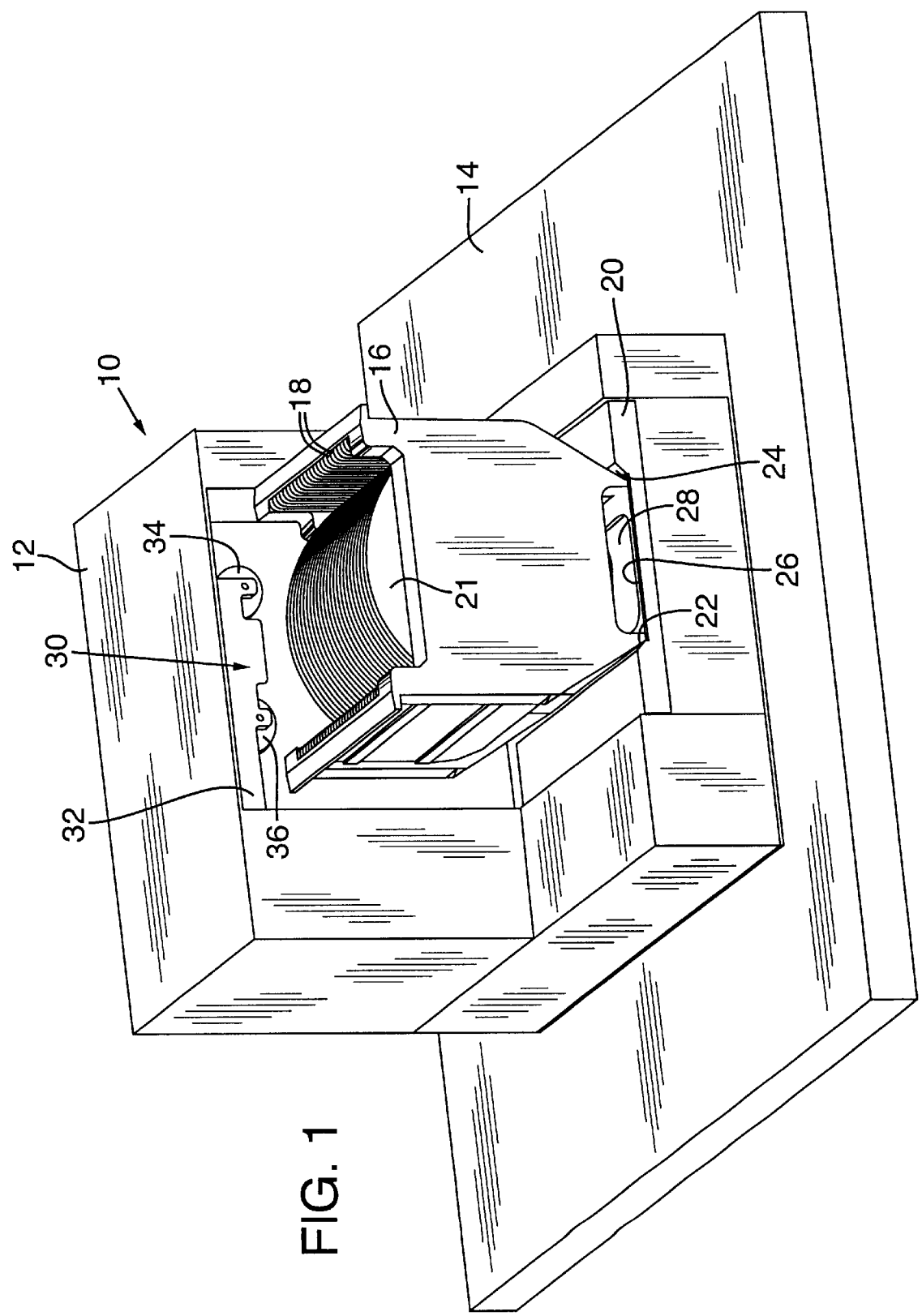
FIG. 1 is a perspective view of one form of an electronic media defect detection apparatus and in particular is illustrated in connection with detecting defects along the side edge margin and outer edge of semi-conductor wafer disks.

FIG. 1 illustrates one form of a defect detector for testing electronic media to determine whether side edge portions and an outer edge of such media contain defects. Although not limited to this specific application, the embodiment shown in FIG. 1 is specifically designed for determining edge defects in disks such as semi-conductor wafers.

More specifically, the unit 10 includes a housing 12 supported by a table or other support 14. In the embodiment of FIG. 1, a cassette 16 is shown. A cassette is a wafer/disk holding and transporting device that holds multiple wafers. Cassettes are typically molded with integrated locating and holding features along with equally spaced guides that define slots within which individual wafers are positioned and held separate from one another. Typical cassettes meet certain industry standards, especially with respect to the location of the first wafer and the spacing of subsequent wafers. In one common approach, cassettes often have an "H" bar, which is a locating device positioned at one end of the cassette and parallel to the first wafer. Two brands of cassettes common are Fluoroware® and Empak®. The cassette 16 includes a plurality of wafer holding slots, two of which are indicated by the number 18 in FIG. 1. Wafers 21 are shown positioned within the slots. Although a cassette may contain any number of wafers, a common cassette includes 25 slots to accommodate up to 25 wafers. The wafers 21 illustrated in FIG. 1 are of a circular configuration, although the invention is not limited to testing electronic media of this specific shape. Cassettes 16 are typically transported either manually by an operator or by a machine. In this case, the cassette is typically supported and transported in the orientation shown in FIG. 1 to prevent the wafers from falling out of the slot openings at the top of the cassette. Removal and/or placement of a cassette from or into the unit may be done manually by an operator. For example, an operator may place his or her hands on the sides of the cassette or gripping tabs on the exposed end of the cassette (depending upon the protocol of the facility), raising the cassette slightly to clear locating features in a cassette support of the unit 10, such as in the upper surface of an index-and-locate platform 20 included in the unit. For example, such features may include first and second sloped walls 22, 24 which help guide the cassette into the platform as well as walls at the end of the platform (one being indicated at 26 in FIG. 1 and at 27 in FIG. 2) to locate the cassette longitudinally on the platform. The cassette may also be placed or removed from the index-and-locate platform 20 by a machine.

As can be seen in FIG. 1, the illustrated cassette 16 has a central open section 28 through which the wafers may be accessed by a wafer lifting apparatus to raise and lower the individual wafers from the cassette during testing. An edge defect sensor assembly 30 is supported by the unit for examining the outer edge and side edge margins of individual wafers when they are indexed into position and raised in proximity to the sensor assembly for testing. In this specific form, the defect sensor assembly 30 is shown supported on an idler arm 32 which is pivotally coupled to the housing 12. Respective first and second rotatable guide pulleys or rolls 34, 36, also carried by arm 32, engage the upper edge of the wafers during the testing procedure.

In the illustrated embodiment with circular disk wafers as the electronic media, the wafers are raised individually into position for testing by the sensor assembly 30 and rotated during testing as explained below. In the event non-disk-like shaped electronic media are tested, a similar sensor assembly may be used with the sensor assembly and media under test being moved relative to one another to in effect scan the edge of the media for defects utilizing the sensor assembly.

Figure 2:
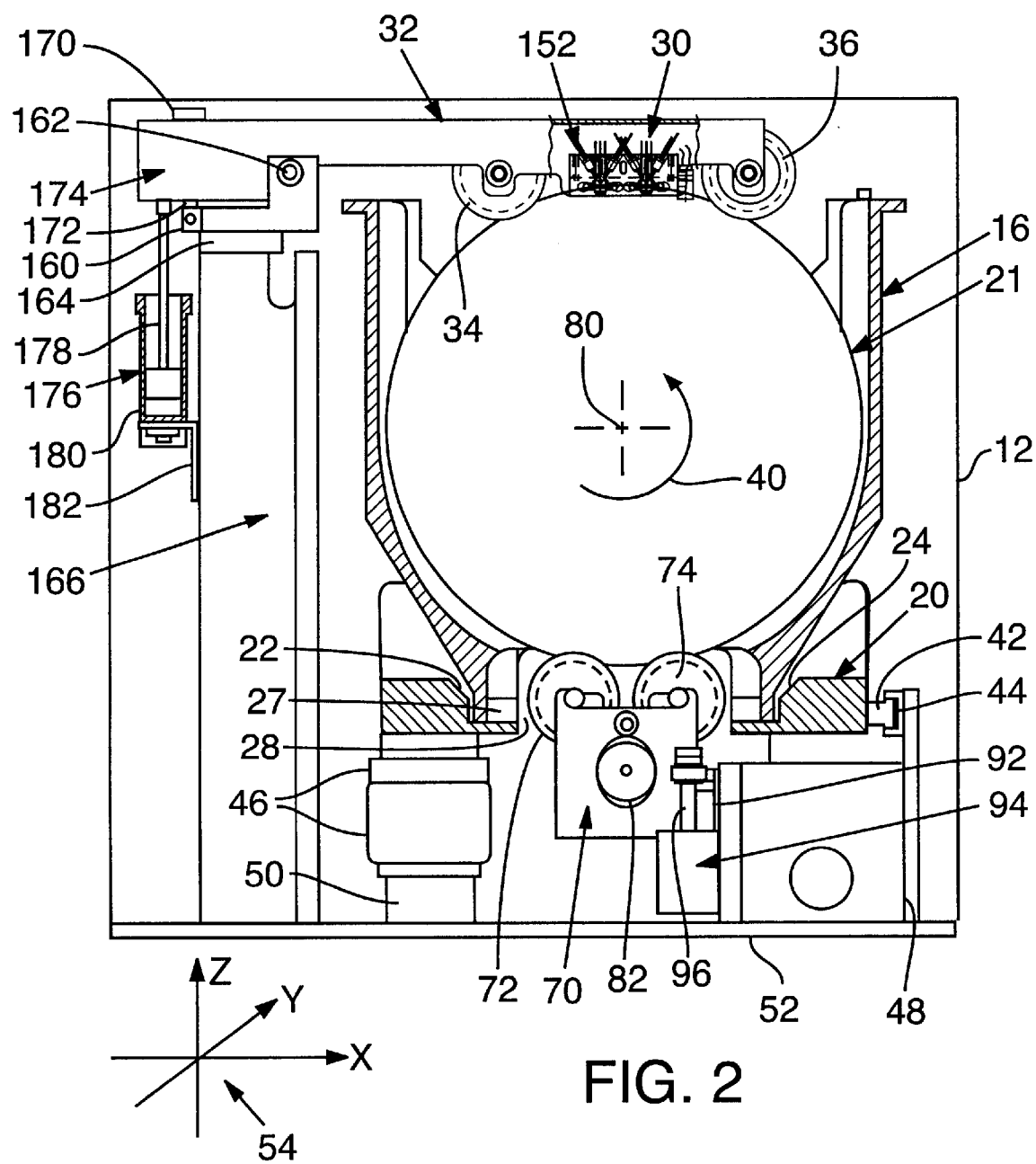
FIG. 2 is a vertical sectional view through a portion of the apparatus of FIG. 1 to illustrate one specific form of such an apparatus.
Figure 3:
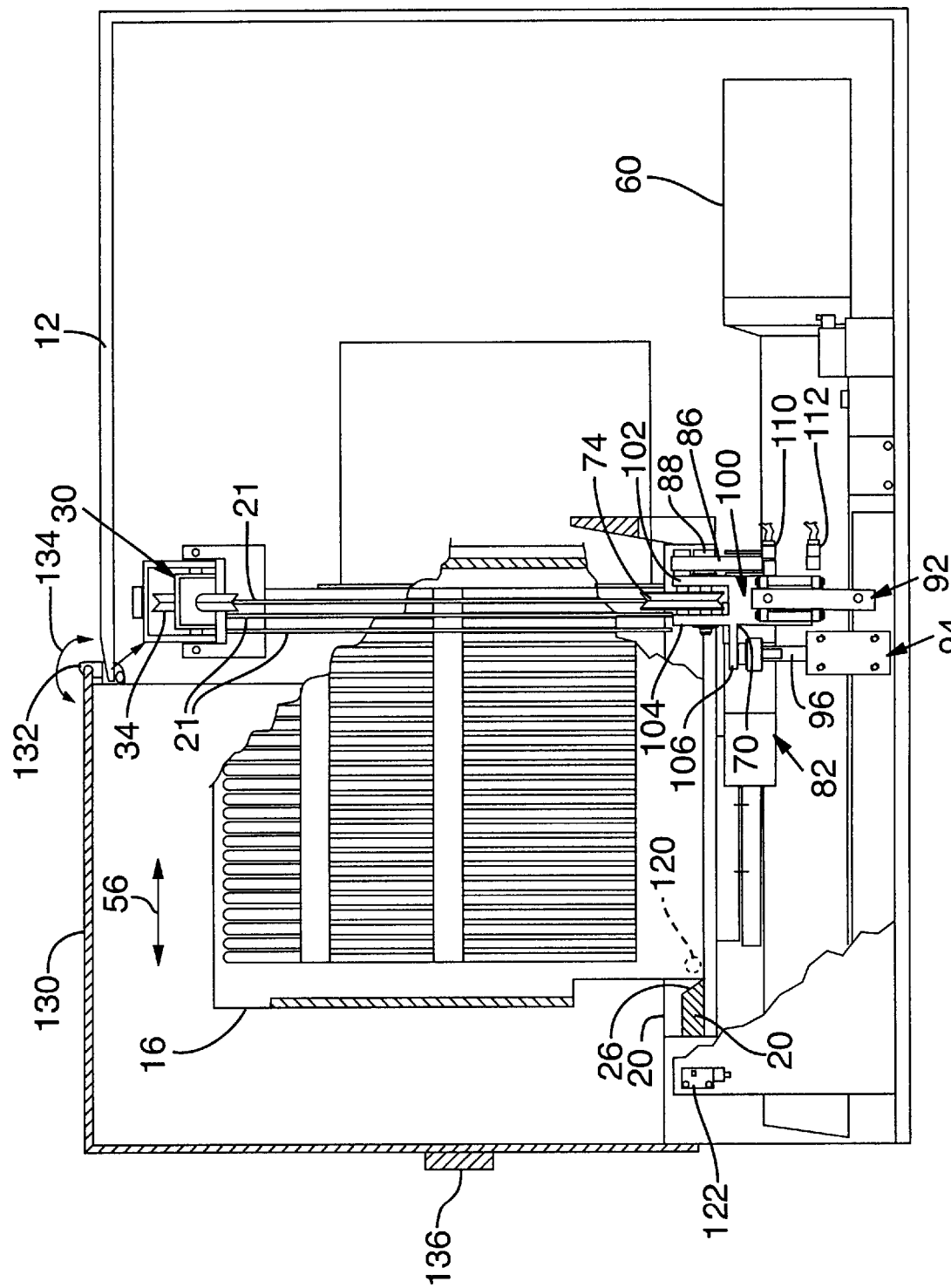
FIG. 3 is a vertical sectional view of the apparatus shown in FIG. 1, taken in a direction which is orthogonal to the direction of the section of FIG. 2, and with portions of the apparatus removed for purposes of illustration.

With reference to FIGS. 2 and 3, one of the wafers 21 is shown in an elevated position for testing with the wafer being driven in rotation, in this example, in the direction indicated by arrow 40 (FIG. 2). In the form shown, platform 20 is supported along one side edge by an elongated slide 42 positioned within a guide rail 44. In addition, the opposite side of platform 20 is supported by a motorized linear slide indicated at 46. Slide 46 and rail 44 are carried by respective upright supports 48, 50 coupled to the bottom 52 of the housing 12. FIG. 2 illustrates a coordinate system 54 having respective x, y and z axes with, in this case, the y-axis extending perpendicularly into the page of FIG. 2. Platform 20 is supported by the slide elements for movement in the y direction toward and away from the sensor assembly. This motion is also shown by the arrow 56 in FIG. 3. In the illustrated embodiment, a motor 60 of the motorized linear slide is controlled by a motor controller (which in turn may respond to computer controls as indicated below) moves the cassette 16 in the y direction to advance and index the wafers into position along the y-axis for testing. As one specific example, the y-axis motorized linear slide with matching motor controller may be an IAI® RC-S5L actuator and an RCA-S controller. The cassette index-and-locate support or platform 20 holds the cassette 16 in a known position when the cassette is positioned by the locating elements of the platform 20. The slide 42 may comprise a bearing carriage that rides in channel 44 with the channel being U-shaped as shown. As a specific example, this assembly may comprise a Rollon® CSW18-100U slider and a ULV-18 Series rail.

In the form shown, the center of the index-and-locate platform 20 has been removed to provide access to the opening 28 at the bottom of the cassette. Consequently, the platform 20 may straddle a wafer lifting and drive mechanism, such as the motorized drive roll assembly indicated at 70 in FIG. 2. The illustrated drive motor assembly 70 is designed to raise the wafer being tested upwardly in the cassette such that the wafer no longer contacts the cassette and, in conjunction with rollers 34, 36, support the wafer reliably for scanning by the sensor assembly 30 for defects. Although mechanism 70 may take other forms, particularly if the electronic media takes shapes other than being circular, in the form shown the assembly includes a first drive roll 72 supported for rotation about an axis which is parallel to the y direction and a second spaced apart drive roll 74 supported for rotation about a axis parallel to the axis of rotation of roll 72. The rolls 72, 74 may comprise two precision ground V-shaped pulleys or drive rollers which capture and rotate the wafer about the center axis 80 of the wafer. Although other materials may be used, rolls 72, 74 may be of 70 to 80 durameter shore A polyurethane. As a result, the lower edge portion of wafer 21 is guided into the grooves of these drive rollers when the rollers are lifted into engagement with the wafer. The drive rollers may be driven by a motor 82, such as a DC gear motor, with a Maxon® 2023 Series motor with/gear head being a specific example. The motor 82 may be coupled to the drive rolls by means of a timing belt 86 (FIG. 3) and belt idler pulley 88. The assembly 70 is coupled to the housing 12 for upward and downward movement in the z direction. Although other mechanisms may be used, in one specific approach, the assembly 70 is carried by a "Z" axis linear slide for supporting and guiding the movement of the assembly 70 upwardly and downwardly. As a specific example, a THK® RSR9 Series linear slide/carriage assembly may be used for this purpose. A mechanism is also provided for raising and lowering the drive assembly 70. Although other forms of elevating mechanisms may be used, such as an electric motor coupled to a drive screw, in the illustrated example a pneumatic cylinder 94 is utilized for this purpose. The housing of the cylinder 94 is coupled to the framework for the unit. In addition, the piston rod 96 of cylinder 94 is positioned to engage the assembly 70 such that extension of the cylinder raises the assembly and retraction of the cylinder lowers the assembly in this specific example. As best seen in FIG. 3, the assembly 70 may include a bracket 100 having upwardly extending bifurcated or spaced apart leg portions 102, 104 which support the respective drive rolls 72, 74. In addition, the bracket 100 may have an outwardly projecting flange portion 106 which is coupled or connected to the upper end of the rod 96 of cylinder 94. Cylinder 94 is typically designed to raise and lower the drive assembly between upper and lower stops (not shown) and thus between respective wafer drive lifted and wafer drive retracted positions. As a specific example, cylinder 94 may comprise a Compact® T12X3/4 double acting air cylinder. A directional air valve may be controlled by a computer to thereby control the operation of the air cylinder and the position of the assembly 70. For example, a Clippard® E4-1ES-24VDC solenoid valve may be used for this purpose with air being delivered to one port of the cylinder to extend the piston rod 96 and raise assembly 70 and to another port of the cylinder to lower the piston rod and retract the assembly.

In the embodiment shown in FIG. 3, first and second sensors 110, 112 are provided for detecting the position of the drive roll assembly 70 in the raised drive position (sensor 110) and in the lowered retracted position (sensor 112). These sensors provide signals to, for example, a computer for use in determining the position of the drive assembly. As a specific example, sensors 110, 112 may be slotted optical sensors such as SUNX® PM-K24 sensors.

Figure 5:
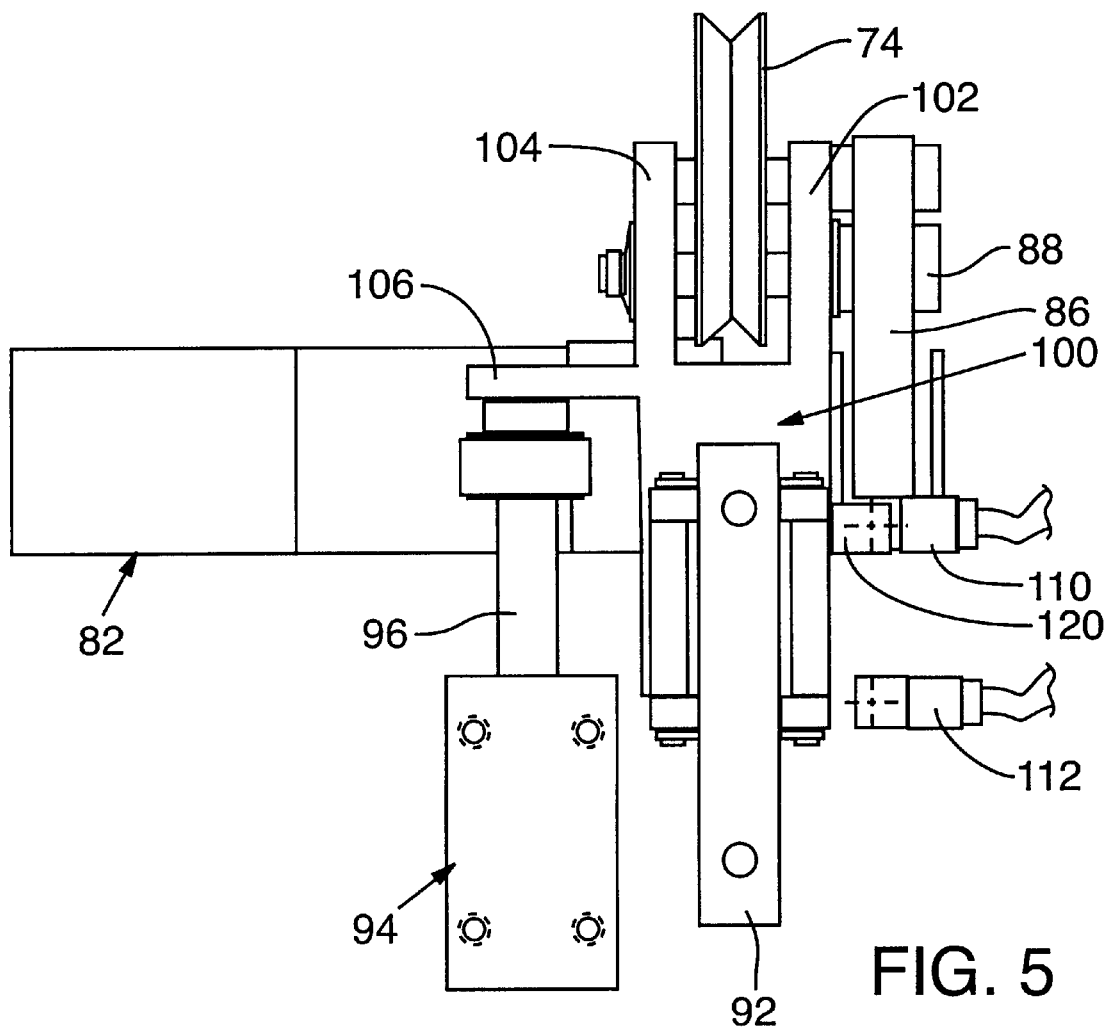
FIG. 5 illustrates one form of a wafer lifting and rotation apparatus usable in the embodiment of FIG. 1 for lifting an individual wafer upwardly from a wafer cassette and for rotating the wafer during defect testing.

FIG. 5 illustrates an enlarged view of the illustrated form of assembly 70 and associated components as discussed above. Like elements to those in FIGS. 2 and 3 have been assigned like numbers in FIG. 5 and will not be discussed further. In FIG. 5, bracket 100 is shown with a flange 120 projecting outwardly to pass between the slots defined by the respective slotted sensors 110, 112. Flange 120 interrupts a beam passing between a respective light emitter and detector of the sensors 110, 112 to indicate the positioning of the assembly 70 in the respective raised and lowered positions.

In FIG. 3, the cassette 16 is shown shifted partially to the right in this figure (in the y direction as indicated by arrow 56) to position the first wafer slot of the cassette in position for testing of a wafer contained therein. More specifically, in FIG. 3, the drive mechanism has been raised to lift this first wafer upwardly away from the cassette 16 so that it may be rotated without engaging the cassette. This minimizes possible damage to the wafer from rubbing against the cassette as well as debris being generated by any such rubbing action. When the illustrated cassette 16 is positioned in its initial unload/load position (see FIG. 1) through openings through the sides of the platform 20 are blocked by the cassette. One such opening 120 in the left side of platform 20 is shown in FIG. 3. When in the load/unload position, a through-beam optical sensor, one portion of which is indicated at 122 in FIG. 3, is in alignment with the opening 120 and the corresponding opening at the opposite side of the platform 20. In other words, when platform 20 is shifted to the left in FIG. 3 to the load/unload position, an optical beam (e.g., from element 122) passes through the openings in the sidewall when no cassette is present. When a cassette is properly positioned in the platform 20 and when the platform is in the unload/load position, the cassette interrupts the optical beam passing between element 122 and a corresponding detector at the opposite side of the platform. The beam is thus broken to indicate the presence of the cassette. A cassette position indicator is optional (for example, an operator can visually determine whether the cassette is properly loaded). Also, other forms of cassette positioners may be utilized.

FIG. 3 also illustrates a cover 130 pivoted at 132 to the housing 12 for pivoting in the direction indicated by arrow 134 between open and closed positions. A cover position sensor may optionally be used to sense and indicate whether the cover is in a closed position. For example, upon detection of the initial opening of the cover, the apparatus may be turned off to prevent, for example, exposure of a worker to moving parts of the unit. In general, cover 130 (which in this case has a handle 136) shields the sensor and detector assembly 30 from ambient light that could interfere with defect detection since the illustrated assembly 30 utilizes light sources and light detectors for edge defect determination. If ambient lighting conditions are constant and are at relatively low intensity levels, then shielding by a cover or other light shielding mechanisms is not necessary. When cover 130 is opened, sufficient clearance is provided along the sides, top and front of the unit 12 to facilitate ergonomic loading of a cassette 16 onto the platform 20. One suitable form of cover closed sensor is a SUNX® PM-K24 sensor. A power supply, not shown, is included to provide 24-volt DC power and other power levels to components included in the unit. Housing 12 contains brackets and framework, such as shown in these figures, to support the various components and sensors therein.

With reference to FIG. 2, although variable, a typical speed of rotation of the wafer 21 being tested is 2 seconds per revolution.

Figure 6:
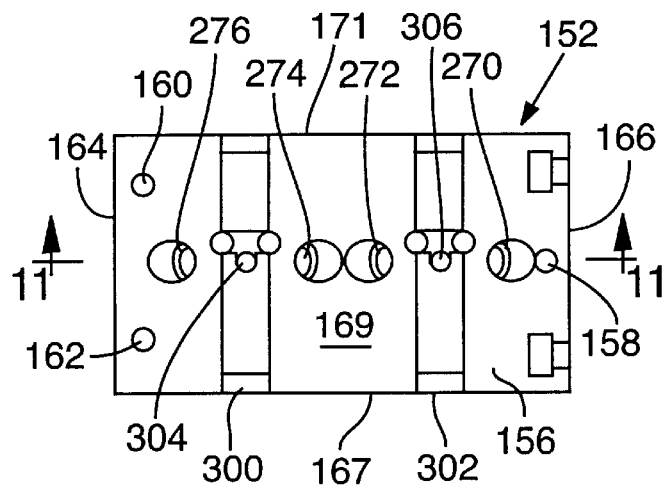
FIG. 6 illustrates a top view of one form of a sensor and detector support for supporting a plurality of light sources and light detectors, such as LEDs which emit visible light and detectors of such light.

As previously mentioned and with reference to FIG. 2, idler arm 32 supports the illustrated sensor assembly 30. The illustrated sensor assembly includes a sensor support 152 which may take the form of a sensor support block 156 as shown in FIG. 6. In this specific example, three threaded bores 158, 160 and 162 are provided at the upper surface 169 of block 156. Bores 160, 162 being adjacent to a first end 164 of the block while bore 158 is adjacent to the opposite end 166 of the block. As can be seen in FIG. 6, these bores provide a three-point mount for the block 156 to the idler arm 32. More specifically, three alignment screws may be captured in idler arm 132 with the screw heads being exposed from above. These alignment screws are threaded into the respective bores 158, 160 and 162. By tightening and loosening these screws (two of which are indicated at 170 and 172 in FIG. 4), the sensor block elevation may be adjusted to position light emitters and detectors supported by the sensor block at the proper elevation for focusing on the desired side edge margins and outer edge of the wafer 21 being tested. The block 156 also has side surfaces 167, 171 and a bottom surface 165. Rolls 34, 36 are typically idler rolls and may be identically configured to rolls 72 and 74. For example, rolls 34, 36 may be "V" grooved idler rolls of a suitable material such as 70–80 durameter shore A polyurethane, with other materials also being possible. The V-groove of these rolls capture the outer edge of the wafer 21 and guide the wafer through the sensing centerline of the edge defect sensor assembly 30 as the wafer is rotated.

Idler arm 32 is typically pivoted to permit the idler arm to move upwardly and downwardly. For example, arm 32 may be pivoted to a pivot support such as a pivot alignment block 160 (FIG. 2) for pivoting about an idler arm pivot axis 162. Support 160 is carried by a support, such as a block 164 positioned at the upper end of an upright idler arm support post 166. Block 164 is typically rigidly connected to support post 166 and provided with elongated slots extending primarily in the x direction. Pivot alignment block 160 is bolted to support 164 with the bolts extending through the slots. When the mounting bolts are loosened, pivot alignment block 160 may be moved in the x direction to align pulleys 34, 36 with pulleys 72, 74 to provide a four point contact with the wafer 21. The wafer 21 is centered by the pulleys 34, 36 at the desired distance (e.g., equal distance) between sensors focusing on the side edges of the wafer. The bolts are then tightened to securely mount pivot alignment block 160 to support 164. A stop 170 carried by the upper end of a shaft 172 which extends through idler arm 32 limits the downward motion of the sensor assembly support portion of the idler arm. The stop 170 prevents the idler arm from lowering below a minimum acceptable position in this example. The idler arm is counterbalanced by increasing the weight of the portion of the idler arm 174 to the left of pivot 162 in FIG. 2. For example, although variable, the idler arm assembly may be counterbalanced so that approximately 20 grams pressure is applied by rolls 34, 36 to the edge of the wafer 21. Movement of the idler arm 32 may also be limited or damped by a damping mechanism such as a damping cylinder 176. As shown in FIG. 2, in this example the rod 178 of cylinder 176 is coupled to the idler arm 32 at the left side of pivot 162 in this figure. The cylinder housing 180 of cylinder 176 is mounted by a bracket 182 to the support post 166. Although variable, as a more specific example, the damping coefficient of damping cylinder 176 may be 0.2 pounds per inch per second. As a specific example, the damping cylinder may be an AIRPOT® S95 Series cylinder. The damping cylinder facilitates low idler roll contact pressure with the edge of the wafer being tested while minimizing any bounce in the idler arm that may otherwise be caused by a defect or wafer notch passing in contact with the various wafer supporting rolls.

FIG. 2a illustrates an alternative form of support for the idler arm 32. In FIG. 2a, components in common with those in FIG. 2 have been assigned like numbers for convenience. In FIG. 2a, the idler arm 32 is supported by a mechanism which facilitates adjustment of the position of the idler arm in x and y directions (see reference coordinate system 54). In addition, a mechanism is also provided to permit rotation of the idler arm about the z axis to facilitate alignment of the upper rollers 34,36 with the drive rollers 72,74 (FIG. 2). In FIG. 2a, one form of the x,y adjustment mechanism is indicated generally at 184 and one form of the z-axis rotation adjustment mechanism is indicated generally at 186. In general, idler arm support 160 is slidably mounted to a base 188 for movement relative to base 188 in both directions along the x-axis within the mechanical limits of the system. An adjustment knob 190 is rotatable relative to support 188 to rotate a drive screw or other base movement mechanism in respective directions to shift platform 160 in the x and −x directions. A set screw 191 may be used to selectively fix the position of support 160 in the desired x position of adjustment. A lower portion of x-position base 188, indicated at 192 in FIG. 2a, may be slidably coupled to a y-position adjustment base 193 such that portion 192 is movable relative to base 193 in the y-direction within the mechanical limits of the adjustment mechanism. An adjustment knob 194 rotatably coupled to y-position base 193 may be rotated in respective opposite directions to drive, for example, a drive screw to shift component 192 and thus the idler arm 32 in the y-directions. A set screw 195 may be used to selectively fix the idler arm in the desired y-position of adjustment. Member 193 is supported by a pivot platform 196 which is rotatable in opposite directions about the z-axis within limits of the system. An adjustment knob 197 drives a rotation drive mechanism, such as a worm gear, coupled to pivot platform 196 to rotate the platform in the desired direction. A pin 198 may be inserted into respective apertures of member 196 to selectively retain the z-axis adjustment mechanism at its desired position of adjustment. The x,y and z-axis adjustment mechanisms 184,186 are typically carried by the post 166. One form of suitable x-y adjustment mechanism is a Model K55-020 x-y-axis metric stages which is commercially available from Edmond Scientific Company. A specific example of a suitable z-axis adjustment mechanism is a Model K55-029 metric rotary stages which is also commercially available from Edmond Scientific Company. Of course, other x,y and z adjustment mechanisms may be used if desired and such mechanisms may be eliminated although this would be less desirable.

In accordance with an optional feature of one embodiment of an edge defect detector, an optional cleaning system is desirably employed to clean the edge of the wafer prior to moving the wafer relative to one or more emitters and detectors. Although such a cleaning system may take a variety of forms, in one specific example, a gas cleaning system such as indicated generally at 181 in FIG. 2a may be employed. Cleaning system 181 comprises a gas nozzle 183 for directing air toward the edge of the wafer 21. Nozzle 183 is located upstream of the sensor assembly 30. Gas from a pressurized source of gas 185, such as nitrogen gas, another inert gas, or clean dry air, is coupled to nozzle 183 through a valve 187 and a flow regulator 189. Valve 187 may open in response to a control signal on a line 201 to permit the passage of pressurized gas from the source to the nozzle. Flow regulator 189 provides a mechanism for adjusting the volume of gas flow and may be used to shut off the gas flow in the event gas bathing of the wafer is not desired. Typically, the control signal 201 is generated in response to raising the assembly 70 (FIG. 3) and lifting of the wafer 21 into position for examination. The computer may cause the generation of the control signal at input 201 when the drive roll assembly 70 is detected in the raised drive position (e.g., by sensor 110).

Figure 4:
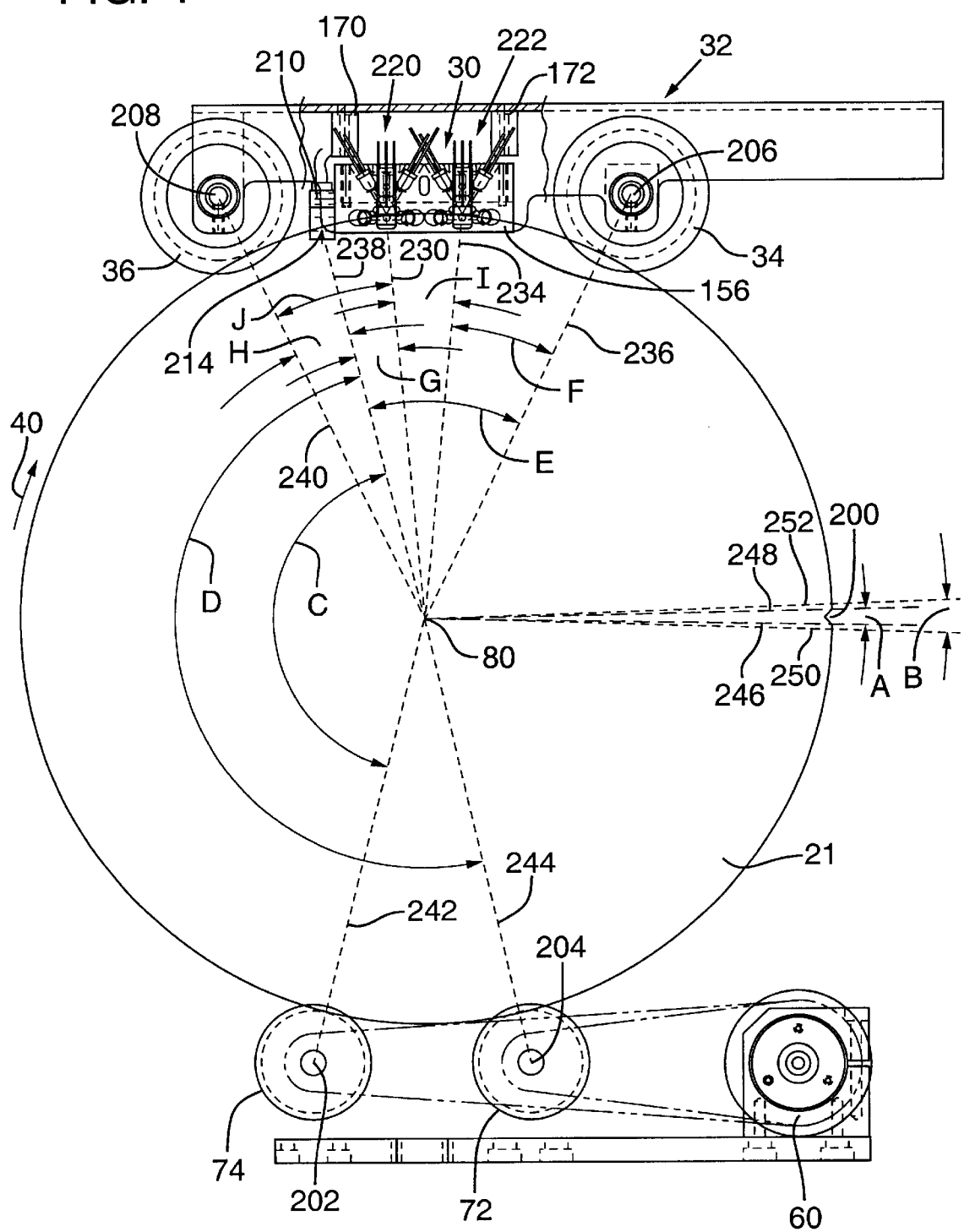
FIG. 4 is an illustration of a portion of the apparatus of FIG. 1 shown in use to evaluate defects in a single semi-conductor wafer disk.

With reference to FIG. 4, which shows a slightly different configuration for the drive rolls 72, 74 and motor 60, one exemplary layout for a specific embodiment in accordance with the present invention is illustrated, it being understood that other configurations may be used. In this specific example, the wafer 21 has a position indicia which can be detected to locate a known position on the wafer. This position indicia may be added prior to testing of the wafer or may be formed during wafer manufacture. In the embodiment shown in FIG. 4, the indicia comprises a notch 200. The axis of rotation of pulley 74 is indicated at 202 in FIG. 4. In addition, the axis of rotation of pulley 72 is indicated at 204. Furthermore, the axis of rotation of pulley 34 is indicated at 206 while the axis of rotation of pulley 36 is indicated at 208. In addition, the illustrated sensor assembly 30 includes an indicia detector 210 which in this case comprises a detector for detecting the passage of notch 200. In one specific form, detector 210 comprises a through-beam slotted sensor which is positioned such that an optical beam is broken by the wafer except when the notch passes through the sensor. As a specific example, notch detector 210 may comprise an SUNX® PMK24 sensor. Notch detector 210 is carried by block 156 at the leading edge of the block, in this example, such that notch 200 passes through detector 210 prior to passing defect sensors carried by block 156. The location of the through beam of this detector 210 is indicated at 214 in FIG. 4.

The block 156 may be machined, molded or otherwise formed to hold a plurality of light emitters, such as Chicago Miniature Lamp, Inc.® No. CMD204UWC emitters or LEDs and a plurality of light detectors (such as TAOS® No. TSL256 detectors). Although fewer or more emitters and detectors may be used than shown in FIG. 4, in the illustrated assembly, two sets of emitters and detectors are provided. The first set is indicated generally at 220 in FIG. 4 while the second set is indicated generally at 222 in this figure. The first set includes six light emitters, two facing the front side edge margin of the wafer, two facing the back side edge margin of the wafer, and two facing the outer edge of the wafer. The first set 220 also includes three detectors with the first being positioned to receive light scattered by defects at the front side edge margin of the wafer, the second being positioned to receive light scattered by defects from the back side edge margin of the wafer and the third being positioned to received light scattered by defects from the outer edge of the wafer to a distance of about 2 mm toward the center of the wafer. The front and rear facing detectors receive scattered light from a wider portion of the side margin of the wafer edge. The respective detectors are focused on specific focal points. The associated two emitters for each detector in this specific example have light energy directed at an angle toward the focal points of the respective detectors. In this example, the absence of a defect, light from the emitters is reflected from the wafer generally in a direction away from the associated detector. In contrast, upon encountering a defect, the light is scattered with some of the light being detected by the associated detector and with the amount of detected light and variations in the detected light being usable to determine the presence of a defect as explained in greater detail below. The location of the focal points of the sets of emitters and detectors 220, 222 in this example are along radial lines 230, 234 in FIG. 4. In addition, the axis 206 of wheel 34 is along radial line 236, the focal point of detector 210 is along radial line 238; the axis 208 of pulley 36 is along radial line 240; the axis of pulley 74 is along radial line 242; the axis 204 of pulley 72 is along radial line 244; the leading edge of notch 200 is along radial line 246; and the trailing edge of notch 200 is along radial line 248. Radial lines 250, 252 are positioned on opposite sides of the respective lines 248, 246 and indicate a portion of the wafer edge that is ignored, in this example, to eliminate distortions caused by notch 200 passing by the respective light emitters and detectors. Obviously the notch 200 rotates as the wafer is driven in rotation.

In this specific example, the angle A between lines 246 and 248 is 2.26 degrees; the angle B between lines 250, 252 is 3.42 degrees; the angle C between lines 238, 242 is 151.57 degrees; the angle D between lines 238 and 244 is 178.95 degrees; the angle E between lines 236 and 238 is 40.75 degrees; the angle F between lines 234 and 236 is 20.56 degrees; the angle G between lines 230 and 238 is 9.29 degrees; the angle H between lines 238 and 240 is 11.27 degrees; the angle I between lines 230 and 234 is 10.89 degrees; and the angle J between lines 230 and 240 is 20.56 degrees. Again, these angles and positions may be varied but provide a suitable example of an edge detector in accordance with one specific embodiment of the present invention.

Referring again to FIG. 2, upon energizing the solenoid valve which controls air flow to cylinder 94, pressurized air is delivered to an appropriate input on the air cylinder to extend piston rod 96 and raise the drive roll assembly 70 upwardly in a z direction. The V-grooved drive rolls 72, 74 engage and center the semi-conductor wafer 21 both in the groove of the rolls and between the rolls while raising the wafer in the z direction. The wafer is raised approximately 9 mm to clear the cassette in this specific example. Before the wafer is raised to its maximum elevation by assembly 70 in the z direction, the wafer enters and is centered by the V-grooves of the two idler rolls 34, 36 which in turn position the edge of the wafer in the sensing centerline of the edge defect sensor assembly 30. This z-axis upward movement of the wafer 21 also raises the idler arm assembly approximately 1 mm, resulting in the application of a light force to the edge of the wafer. At the maximum raised position, both the drive rolls 72, 74 and the idler rolls 74, 36 combine to make a near perfect 4-point contact with the outermost edge of the wafer while positioning the wafer edge in the correct location for measurement by the edge defect sensor assembly 30. This 4-point wafer contact virtually eliminates any wafer bounce that could otherwise occur when the wafer notch 200 contacts an idler or drive roll if a 3-point contact system were used. However, a 3-point or other contact system could be used, although less desirable. Other wafer supporting mechanisms may also be used. Also, although less desirable, the wafer could be rotated without lifting the wafer from the cassette. The grooved idler and drive rollers provide self-centering and alignment of the wafer being tested. In addition, this method of supporting the wafer during testing substantially eliminates contact with the front or back sides of the wafer. In addition, in the illustrated approach, no contact occurs between the wafer cassette and wafer during testing of each individual wafer. Moreover, the wafers need not be removed from the cassette slots during testing. However, in an alternative embodiment, wafers may be tested individually without a cassette. For example, the wafers may simply be placed on the drive rolls (for example utilizing a vacuum wand), raised into position and then tested. As is also apparent from FIG. 1, when cassettes are used, they may be placed directly onto the apparatus without the need to be rotated by an operator or another mechanism prior to placement in the apparatus for subsequent testing.

Although not required, redundant sensors such as sets 220, 222 may be provided for front, back and top edge wafer defect detection. For example, the focal points of the sensors may be offset from the center 80 of the wafer so as to direct light and detect light toward the wafer at different angles. For example, four angles of emitter emission may be provided along the front edge margin of the wafer, along the back edge margin of the wafer, and along the top edge of the wafer. Multiple angles of emitter emission increases the ability of the system to detect minute defects. In addition, the use of redundant sensors and emitters allows for the removal of anomalies that may be caused, for example, by the wafer notch touching one of the idler or drive rolls. For example, the system will know when a notch passes a roller and thus can ignore readings for a particular location along the wafer from a first set of sensors at this time. Data for this position along the wafer may then be read by the second set of sensors when the notch is no longer engaging a drive idler roll. This data can then be inserted into the data stream in place of the ignored data that would have been gathered by the first set of sensors at a time when the notch is engaging one of the rolls.

Yet another form of sensor support 152 may be used, such as the sensor support block illustrated in FIGS. 27–30. These figures correspond to FIGS. 6, 7, 9 and 12. Common components in these respective figures have been assigned the same number for convenience and will not be discussed further.

Figure 7:
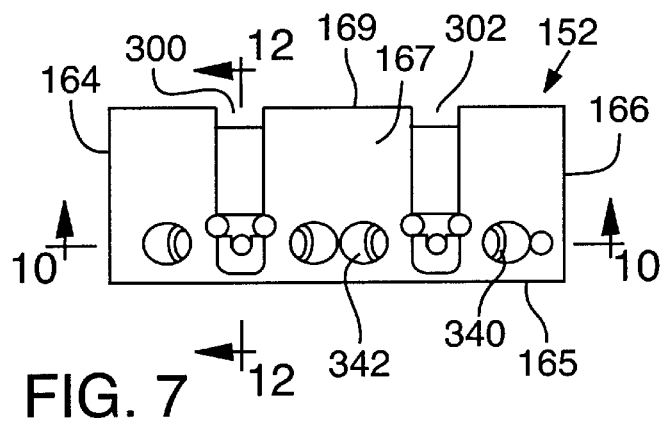
FIG. 7 is a side elevation view of the support of FIG. 6.
Figure 8:
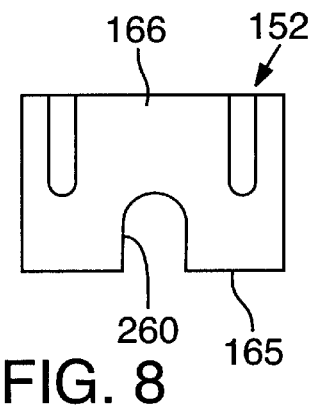
FIG. 8 is an end view of the support of FIG. 6.
Figure 30:
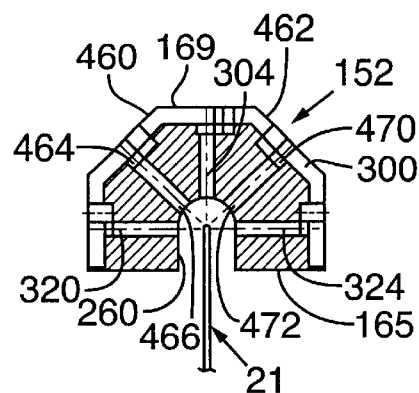
FIG. 30 is an vertical sectional view of the support of FIG. 28 taken line 30—30 of FIG. 28.

In FIGS. 27–30, the respective upper corners of the support 152 of the FIGS. 6 and 7 form have been removed to produce respective first and second beveled surfaces 460,462. Surface 460 extends between side surface 167 and top surface 169 while surface 462 extends between side surface 171 and the top surface. Although not limited to a particular angle, desirably the surfaces 460,462 are at a 45 degree angle with respect to horizontal, such as relative to the top surface 169 if it constitutes a horizontal surface. A light detector receiving bore 464 extends from groove 300 adjacent to surface 460 to the groove 260 and communicates with the groove 260 through an opening 466 which, as can be seen in FIG. 30, is midway between the openings leading from the respective bores 304,320 to the groove 260. Similarly, a bore 470 extends from groove 300 adjacent surface 462 to the groove 260 and communicates with the groove 260 through an opening 472 positioned midway between the openings leading from bores 304 and 324 to the groove 260. The longitudinal axes of bores 464,470 are aligned with respective focal points at the respective upper side edge margin portions of the wafer 21 (see FIG. 30). The angles maybe varied and are typically selected to provide multiple angles of attack of light toward the edge margin of the wafer being tested to minimize the possibility of missing defects. Similarly, a detector receiving bore 472 extends from groove 302 adjacent surface 460 to the groove 260. In addition, a detector receiving bore 480 extends from a location adjacent surface 462 and in groove 302 to the groove 260. Bores 474,480 may be aligned in the same manner as bores 464,470 although their longitudinal axes would be aligned with respective focal points at opposite upper side edge margin portions of the wafer 21 which differ from the focal point of the axes of bores 464,470.

A set of light source receiving bores 482,484 extend inwardly from surface 460 to the groove 260 and communicate with the groove 260 through respective openings. The longitudinal axes of bores 482,484 and of bore 472 intersect at a common focal point. A set of bores 486,488 extend inwardly from surface 460 and communicate with groove 260 through respective openings. The longitudinal axes of bores 486,488 and of bore 464 intersect at a common focal point. In addition, a set of bores 490,492 extend from surface 462 and communicate through respective openings with the groove 260. The longitudinal axes of bores 490,492 and of bore 480 intersect at a common focal point. Also, a set of bores 494, 496 extend from surface 462 and communicate with groove 260 through respective openings. The longitudinal axes of bores 494,496 and of bore 470 intersect at a common focal point. Thus, FIGS. 27–30 illustrate a support with additional sets of respective light delivery bores and associated light detection bores.

The diameter of the bores of the sensor support blocks may vary and they are not required to be the same. However, a typical diameter is 0.063 inch. All or selected bores, for example those associated with the detectors, may be roughened or textured to minimize light at other than the angles of interest being reflected along the walls of the bores. In one form of texturing, the bores are tapped to form threads in the bore walls. Threads at a pitch of 0.4 mm which are deep enough to remove the otherwise flat surfaces of the bores are a specific illustrative example. This texturizing reduces the amount of spurious light that travels to the detectors.

The damping mechanism, such as the damping cylinder 176, attached to the sensor assembly supporting arm 32 enables very light idler roll contact with the wafer edge while minimizing the possible bouncing of the idler arm 32.

Thus, in the embodiment described above positive detection of the wafer notch is accomplished utilizing a slotted optical sensor. In addition, the illustrated system does not require the total removal of wafers from a wafer holding cassette for separate inspection and as a result facilitates a higher throughput of inspected wafers.

Although other energy sources such as lasers, light sources that are split or otherwise divided into plural light sources and ultrasonic emitters or sensors may be used, the embodiment described above desirably may utilize inexpensive visible light emitters and inexpensive light to voltage/current converters. This simplifies the electronics involved in the system and also reduces the costs of the system. For example, as explained below, the electronics may consist of 3 resistors, 3 manually adjusted or digitally adjusted potentiometers for controlling emitter intensity and an off-the-shelf analog to digital card which plugs into any standard PC to provide data from the light detectors in a form usable for processing by the computer.

Figure 9:
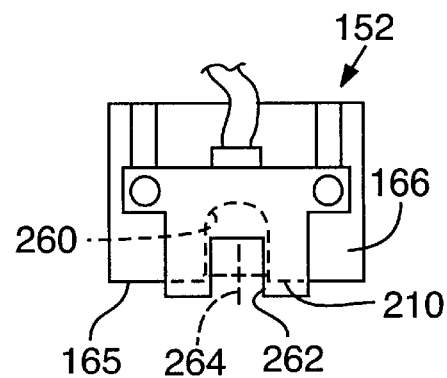
FIG. 9 is an end view of the support of FIG. 6 with a wafer edge indicia detector for detecting a notch or other indicia to indicate a reference position on the wafer.
Figure 10:
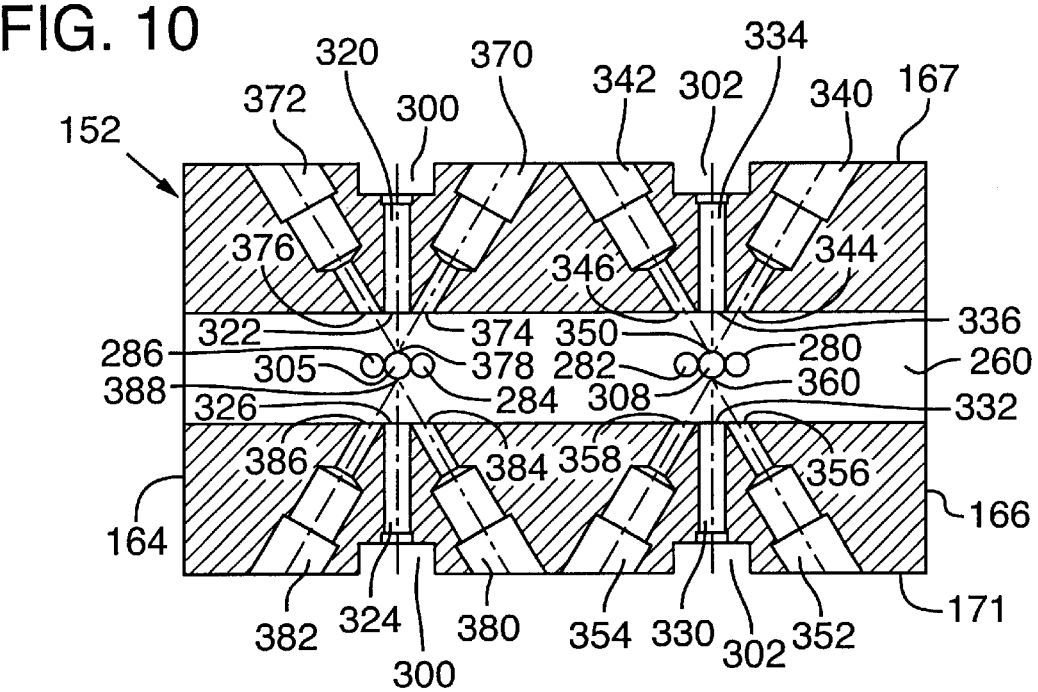
FIG. 10 is a horizontal sectional view taken along line 10—10 of FIG. 7.
Figure 11:
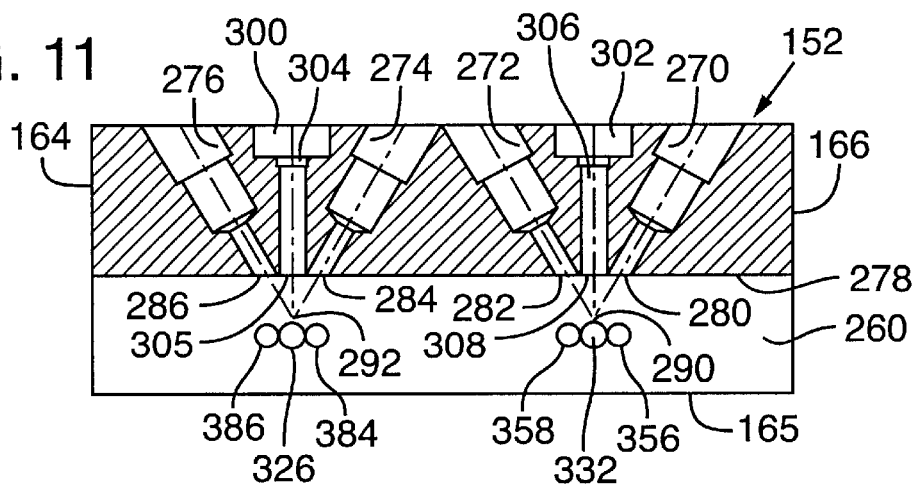
FIG. 11 is a vertical sectional view of the support of FIG. 6, taken along line 11—11 of FIG. 6.

The illustrated form of sensor support 152 and sensor assembly 30 is best seen with reference to FIGS. 6–15. In the illustrated form, sensor support 152 comprises the sensor support block 156 which is provided with a longitudinally extending groove extending inwardly into the block 156 from the bottom surface 165 of the block, this groove being indicated at 260 in some of these figures. As can be seen in FIG. 9, the notch detector 210 has a slot 262 which is aligned with groove 260 when notch detector 210 is mounted, such as by screws, to the end 166 of block 152. The centerline of slot 262 and of groove 210 is indicated at 264 in FIG. 9. As can be seen in FIGS. 6, 11 and 13, the illustrated block 156 includes a first set of bores 270, 272 and a second set of bores 274, 276. These bores communicate from the upper surface 169 of block 156 to the groove 260. More specifically, the bores 270, 272, 274 and 276 communicate with the groove 260 through respective openings 280, 282, 284, and 286. The longitudinal axes of bores 270, 272 intersect at a focal point location 290 as explained below. In addition, the longitudinal axes of bores 274, 276 intersect at a focal point 292. Although variable, the angles between the longitudinal axis of bore 270 and bore 272 may be sixty degrees and the angle between the longitudinal axis of bore 274 and bore 276 may also be sixty degrees.

Figure 12:
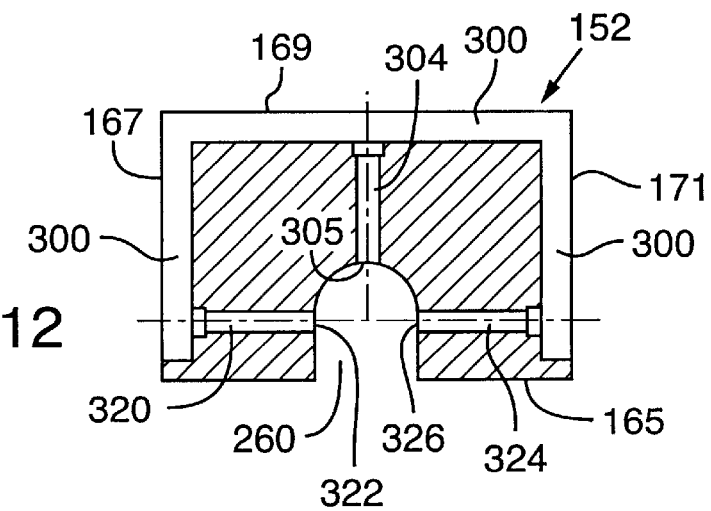
FIG. 12 is a vertical sectional view of the support of FIG. 7, taken along line 12—12 of FIG. 7.

As best seen in FIGS. 6, 7, and 12, spaced apart grooves 300, 302 may be provided in block 156. Each of these grooves may extend from a location adjacent to, but spaced from, the lower surface 165 of block 156, along the side surface 167 of the block, across the top surface 169 of the block and downwardly along the opposite side surface 171 of the block to a location adjacent to, but spaced from, the lower surface 165. A bore 304 extends from groove 300 to the groove 260 and communicates with groove 260 through an opening 305 which, as can be seen in FIG. 11, is midway between openings 284 and 286. Similarly, a bore 306 extends from groove 302 to groove 260 and communicates with groove 260 through an opening 308 positioned midway between the openings 280 and 282. The longitudinal axis of bore 306 is aligned with the focal point 290. Similarly, the longitudinal axis of bore 304 is aligned with focal point 292. It should be noted that the angle between the longitudinal axes of bores 274, 276 may be the same as the angle between the longitudinal axes of bores 270, 272 or the angles may differ. The angles are typically selected to provide multiple angles of attack of light toward the edge of the wafer being tested to minimize the possibility of missing defects.

As also can be seen from FIG. 12, a bore 320 extends inwardly into the block 156 from groove 300 at side surface 167 and communicates with groove 260 through an opening 322. In like manner, a bore 324 extends inwardly from groove 300 at side surface 171 and communicates with groove 260 through an opening 326. Bores 320, 326 are also shown in FIG. 10. Bores 324 and 320 have longitudinal axes which are spaced ninety degrees from the longitudinal axis of bore 304. In the same manner a bore 330 extends inwardly from groove 302 and surface 171 to groove 260 with bore 330 communicating with groove 260 through an opening 332. A bore 334 extends inwardly from groove 302 and surface 167 to groove 260 and communicates with groove 260 through an opening 336. A first set of bores 340, 342 extend inwardly from surface 167 to groove 260 and communicate with the groove 260 through respective openings 344, 346. The longitudinal axes of bores 340, 342 and of bore 334 intersect at a focal point 350. A set of bores 352, 354 extend inwardly from surface 171 and communicate with groove 260 through respective openings 356, 358. The longitudinal axes of bores 352, 354 and 330 intersect at a focal point 360. In addition, a set of bores 370, 372 extend inwardly from surface 167 and communicate through respective openings 374, 376 with the groove 260. The longitudinal axes of bores 370, 372 and bore 320 intersect at a focal point 378. In addition, bores 380, 382 extend from surface 171 inwardly and communicate with groove 260 through respective openings 384, 386. The longitudinal axis of bores 380, 382 and of bore 324 intersect at a focal point 388. The angles between respective bores 340, 342; 352, 354; 370, 372; and 380, 382 may be the same as the angles between respective sets of bores 270, 272 and 274, 276. Alternatively, the angles may be varied. In addition, additional bores may be provided to accommodate additional light emitters and detectors at other angles of attack for further refinement of the wafer edge defect detection.

With reference to FIG. 13, the illustrated set 220 of light emitters and detectors include first and second light emitters 400, 402 positioned within respective bores 270, 272 and a light detector 404 positioned within bore 306 for detecting light scattered from the outermost edge of wafer 21 upon the occurrence of a defect. Light emitters 400, 402 and detector 404 are focused on focal point 290. In the absence of a defect, light from emitters 400, 402 is substantially reflected away from detector 404.

The set 220 also includes light emitters 410, 412 (FIG. 14) positioned in respective bores 340, 342 and a light detector 414 positioned within bore 334. Emitters 410, 412 and detector 414 are directed toward focal point 350 along a first side edge margin of the wafer 21. In addition, the set 220 includes light emitters 416, 418 positioned in respective bores 352, 354 and a light detector 420 positioned within bore 330. Emitters 416, 418 and detector 420 are directed toward focal point 360 and thus inspect the opposite side edge margin of the wafer from the side edge margin inspected by emitters 410, 412 and detector 414. The set 222 of emitters and detectors includes a first light emitter 430 positioned within bore 274, a second light emitter 434 positioned within bore 276 and a light detector 436 positioned within bore 304. Light emitters 430, 434 and light detector 436 focus on focal point 292. The set 222 in this embodiment also include light emitters 438, 440 positioned within respective bores 370, 372 and a light detector 442 positioned within the bore 320. Light emitters 438, 440 and light detector 442 are focused on focal point 378 (FIG. 14). In addition, the set 222 includes light emitters 444, 446 positioned within respective bores 380, 382 and a light detector 448 positioned within the bore 324. The light emitters 444, 446 and light detector 448 are focused on focal point 388.

In the sensor and detector support embodiment depicted in FIGS. 27–30, light emitters (not shown) may be positioned in respective bores 482, 484 and a light detector (not shown) positioned within bore 472. These emitters and detectors are directed toward a respective focal point along a first side edge margin of wafer 21. Additional light emitters (not shown) may be positioned in respective bores 486, 488 and a light detector (not shown) positioned within bore 464. These emitters and detectors are directed toward a different focal point at the first side of the wafer and thus are used to inspect another portion of the first side edge margin of the wafer. Also, light emitters may be positioned in the respective bores 490, 492 and an associated detector may be positioned in bore 480. These emitters and detectors are directed toward yet another focal point, in this case, at the opposite side of wafer from the detector positioned in bore 472. In addition, light emitters may be positioned respectively in bores 494, 496 and a light detector may be positioned in bore 470. This detector and these light emitters are focused on an additional focal point located at the second side of the wafer opposite to the focal point to which the detector in bore 464 is directed. With this construction, the emitters in bores 488, 486 and 494, 496 as well as the detectors in respective bores 464, 470 thus constitute additional light emitters and detectors in the first set 220 of light emitters and detectors. In addition, the light emitters in respective bores 482, 484 and 490, 492 together with the light detectors in respective bores 472 and 480 comprise additional emitters and detectors of the second set 222 of light emitters and detectors.

FIG. 15 illustrates the focusing of light detector 442 on one side edge margin of wafer 21; the focusing of light detector 448 on the opposite side edge margin of wafer 21; and the focusing of detector 436 on the outer edge of wafer 21.

Again, the numbers and locations of the various detectors and emitters may be varied. Although other supports may be used for supporting the desired emitters and detectors, a machined or molded block 156 is extremely reliable and can be readily manufactured.

Figure 16:
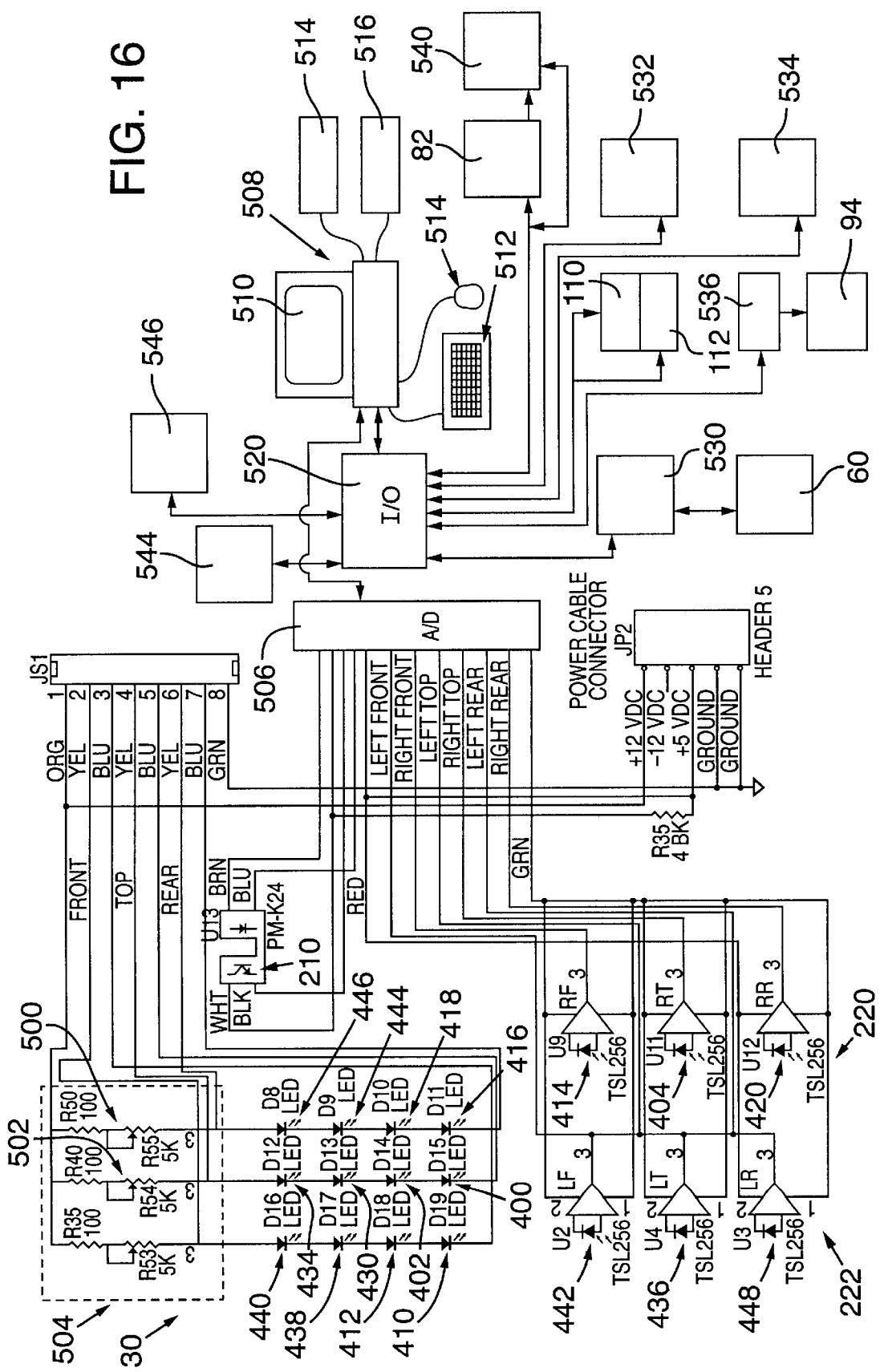
FIG. 16 illustrates an exemplary circuit diagram, partially in schematic form, for use with the defect detector of FIG. 1.

FIG. 16 illustrates one form of circuit schematic diagram and associated components which may be used in connection with the embodiment described above.

The output of the exemplary light detectors may, for example, range from 0 to 4.5 volts. In a specific example, it is desirable to adjust this output to be somewhere in the mid-range when no defect is being detected, for example from about 2 to 2.5 volts. In the illustrated embodiment, respective potentiometers 500, 502, 504 may be adjusted to adjust the output of the light emitting diodes along the front side, top side and rear side of the sensor assembly 30. Potentiometers 500, 502 and 504 may be manually adjusted or may comprise digitally controlled potentiometers. One way of calibrating the system is to run a test utilizing a wafer which is known to contain no defects. The system can then be adjusted such that the detectors produce an output in the desired range. The outputs of the detectors 404, 414, 420, 436, 442 and 448 as well as of the notch detector 210 may be fed to an analog to digital card (A/D) 506 which may be plugged into a conventional computer such as a personal computer indicated at 508.

As an option, another form of a mechanism for automatically or semi-automatically adjusting light intensity from the light emitters may be employed. This may be used to compensate for variations in wafer surface reflectivities arising from wafer manufacturing processes. For example, the front and rear surfaces of a wafer may have different reflectivities. Light emitter intensity adjustment may be performed on one or more of the wafers in the cassette, for example on the first wafer in each cassette or all wafers in each cassette.

Figure 16A:
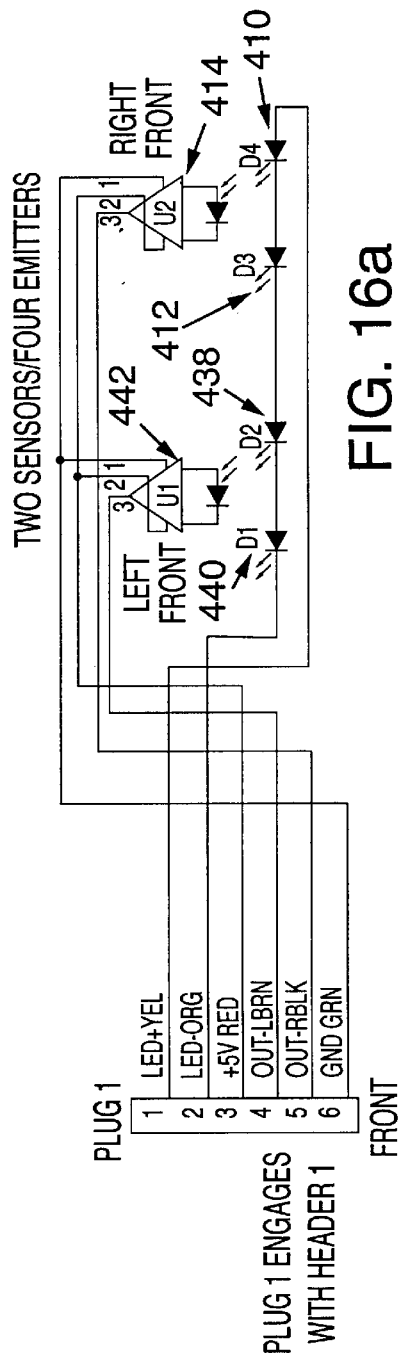
FIGS. 16a and 16b are exemplary circuit diagrams of one form of a light source intensity control for use with the defect detector of FIG. 1.
Figure 16B:
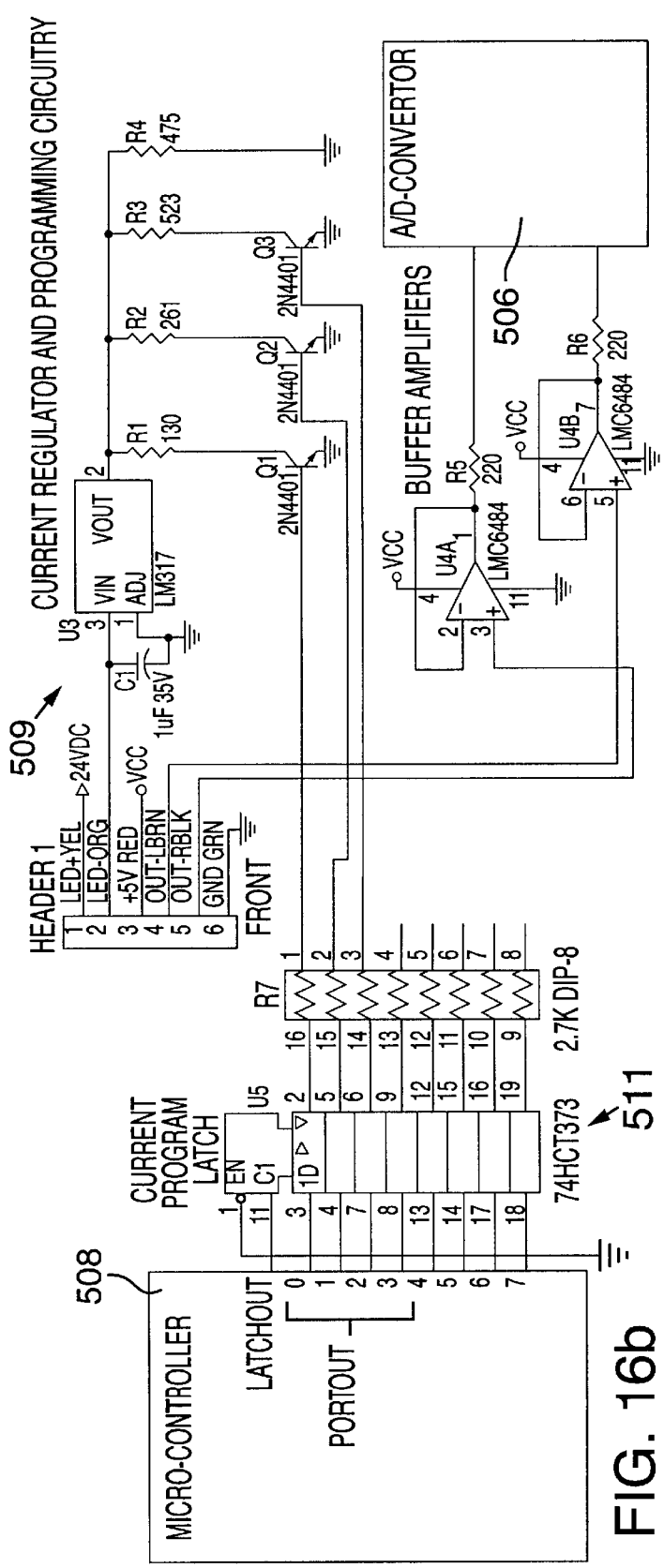

In the exemplary form of intensity adjustment mechanism shown in FIGS. 16a and 16b, for example, one of eight intensities is selected for groups of one or more detectors and their associated emitters. For example, the emitters and detectors focused on the same general edge margin portion of the wafer may be grouped together as the wafer reflectivity for these groups is expected to be the same. As a specific example, for the support 152 shown in FIG. 28, the emitters and detectors associated with surface 167 may be grouped together, those associated with surface 460 may be grouped together, those associated with surface 169 may be grouped together, those associated with surface 462 may be grouped together and those associated with surface 171 may be grouped together. Other groupings may be used. Also, the intensity of individual emitters or those emitters associated with a particular detector may be independently adjusted.

In FIGS. 16a and 16b, an exemplary circuit is shown for adjusting the intensity of several detectors and their associated emitters. This same circuit may be used for other emitter detector groupings for which intensity control is desired. A wafer (e.g., the first wafer in a cassette) is positioned for examination. The outputs of detectors from the group of emitters and detectors which are to be intensity adjusted are monitored. In this exemplary case, the illustrated group consists of emitters and detectors positioned in bores at surface 167 of the support 152 (see FIGS. 10 and 14). That is, the group consists of detector 414 and respective associated emitters 410,412 (which are the source of light detected by detector 414) and detector 442 and respective associated emitters 438,440 (which are the source of light detected by detector 442).

More specifically, in one example, one of a plurality of adjustments is selected, such as one of eight current values is selected by turning on a selected combination of paralleled transisters $Q_1$ and $Q_2$ and $Q_3$ in response to latch output signals from computer 508 to a latch 511. The levels correspond to $Q_1$ and $Q_2$ and $Q_3$ (off the circuit path then being through resistor $R_4$); $Q_1$ on with $Q_2$ and $Q_3$ off; $Q_2$ on with $Q_1$ and $Q_3$ off; $Q_3$ on with $Q_1$ and $Q_2$ off; $Q_1$ and $Q_2$ on with $Q_3$ off; $Q_1$ and $Q_3$ on with $Q_2$ off; $Q_2$ and $Q_3$ on with $Q_1$ off; and $Q_1$, $Q_2$, and $Q_3$ all being on.

The computer 508 may include a display 510, such as a monitor. In addition, the computer 508 may include a data entry device which may take any convenient form. For example, the data entry device may be one or more of a touch screen, a keyboard 512 and/or a mouse 514. Peripherals such as a printer 514 and a hard drive 516 containing additional memory for data storage may be included in a conventional manner. Computer 508 may also be loaded with a conventional operating system. Data from the light detectors and the notch detector may be periodically sampled and stored under the control of computer 508. One or more input/output cards (I/O cards) may be utilized in the system. The A/D and I/O card functions may be provided in the same card or cards with a National Instruments® No. 6034E card being one such example. A schematically represented I/O card is indicated at 520 in FIG. 16. Card 520 converts control signals from computer 508 into a form suitable for various components under the control of the computer and also converts signals from the components of the system to a form suitable for processing by the computer. The components under computer control may include a y-axis controller 530 to control the y-axis motor 60 (FIG. 3) to cause the wafer cassette to index to desired wafer slots and to return to the load/unload position at desired times. The output from cassette presence sensor 532 is also monitored by the computer to determine whether a cassette is present in the system when the system in the load/unload position. For example, in the embodiment of FIG. 3, element 122 is one component of an exemplary presence detector. In the event a door 130 (FIG. 3) is used, a door closed sensor 534 may produce an output which is monitored by the computer to determine whether the door 130 is closed and to also determine when opening of the door commences.

In addition, the computer 508 may be coupled to wafer lifter raised and lowered position sensors 110, 112 (FIG. 3) for purposes of monitoring whether the wafer lifter assembly 70 is raised or lowered. Computer 508 may also control the mechanism used to raise and lower the wafer lifter assembly 70. Thus, one embodiment, the computer may control a valve 536 which causes the cylinder 94 (FIG. 3) to raise and lower the wafer lifter. In addition, computer 508 may control the drive motor 82 (FIG. 3) used to drive rolls 72, 74 and rotate the wafer which is to be inspected. An optional encoder 540 may provide feedback to the computer on the position of drive motor 82 which can be used by the computer to determine the position along the wafer where defects are detected. This also allows accurate positioning of the wafer in a cassette following testing. As a specific example, the wafer may be rotated to position the wafer notch at a desired position such as the 12 o'clock or vertical position following testing. In this case, each wafer can be positioned in a similar manner to facilitate downstream processing of the wafers. Alternatively, the wafers may be rotated to position specific detected defects at a given position, such as the 12 o'clock position to facilitate further inspection of these defects. A conventional camera and controller, indicated at 544, may also be controlled by the computer. More than one camera may be utilized if desired. Thus, for example, once defects have been determined to exist in a wafer, the wafer may be positioned by the computer (e.g., by rotation of the wafer to position the defect at a known position to, for example, correspond with the focus of the camera), such that the camera can be utilized to remotely inspect the defects to determine whether they are indeed significant. A camera or optical character recognition (OCR) vision system may be used in connection with scanning and entering bar code or other indicia which identifies the particular cassette which carries the wafers being examined. Other cassette ID determining systems may also be used. Such systems, although not required, can be used to track the cassette location throughout the wafer production and evaluation process. Also, a conventional vacuum wand and controller indicated at 546 may be controlled by the computer to grasp and remove a wafer determined to have defects. In this case, the housing 12 (FIG. 3) may be modified to permit the operation of such a wand within the housing. In addition, a second cassette may be included in the housing for receiving defective wafers. The defective wafers may be oriented again in a known position prior to delivery to the separate cassette. In this way, the defective wafers may be separated for subsequent visual inspection if desired with wafers passing the inspection remaining in the original cassette where they can be transferred for downstream processing.

As one specific processing approach, as the wafer edge and detectors are moved relative to one another, such as by rotation of the wafer, the wafer is monitored to determine the presence of a position indicia such as a notch. Following the occurrence of the first notch present signal (as determined from signals from notch detector 210) all of the light detectors (e.g., the edge defect light detectors and notch sensor) are typically read as simultaneously as possible and at a sufficiently high sample rate (such as 1000 samples per second) to detect fluctuations in detector outputs caused by edge defects. Sensor sampling may be stopped upon receiving the second notch present signal corresponding to one full rotation of the wafer. The tests may be repeated for additional rotations and the results averaged or otherwise combined if desired. If only a portion of the wafer edge is to be sampled, sampling can stop at a different time. The number of actual samples taken in one wafer rotation is then determined. In this example, the voltage samples from the notch detector are examined for the first transition from a high value (e.g., over 2.5 volts) to a lower value (e.g., under 2.5 volts) to determine the first detection of the notch. The notch voltage samples are then searched for the second transition from a high value to a low value to indicate the second detection of the notch. The number of samples between the first and second notch transitions is the number of samples in one rotation.

The light detector output samples are then analyzed for the purposes of determining the presence of edge defects. Such defects show up as spikes in the voltage values. Although other analytical approaches may be used, in one specific approach, adjacent samples are compared with differences greater than a threshold value being noted. More specifically, the first differential of the output voltage sample values may be determined. The defect threshold may be adjustable, e.g., by input to the computer, to control the sensitivity of the system. Adjustments may be made, for example, to accommodate testing of different types of electronic media and/or wafer samples and also in accordance with the protocol of the particular manufacturing plant. The threshold may be established empirically. As one way of establishing a defect threshold, one can run tests of a non-defective wafer or other electronic media and also of a defect-containing wafer. The threshold can then be adjusted until the defective wafer or media is identified without identifying the good wafer or media as being defective. A default threshold may be established by the software program and may be the same or different for various media types. Typically the comparison operation begins a given number of samples after the first high-to-low transition of the notch sensor signal. In this way, the analysis starts after the notch has passed the wafer edge defect determining detectors. The comparison operation is typically stopped a given number of samples after the second high-to-low transition of the notch sensor signal. This stops the analysis before the notch returns to the edge defect detecting sensors. For example, with reference to FIG. 4, samples between lines 250 and 252 may be ignored as this corresponds to a notch edge exclusion zone.

Figure 17:
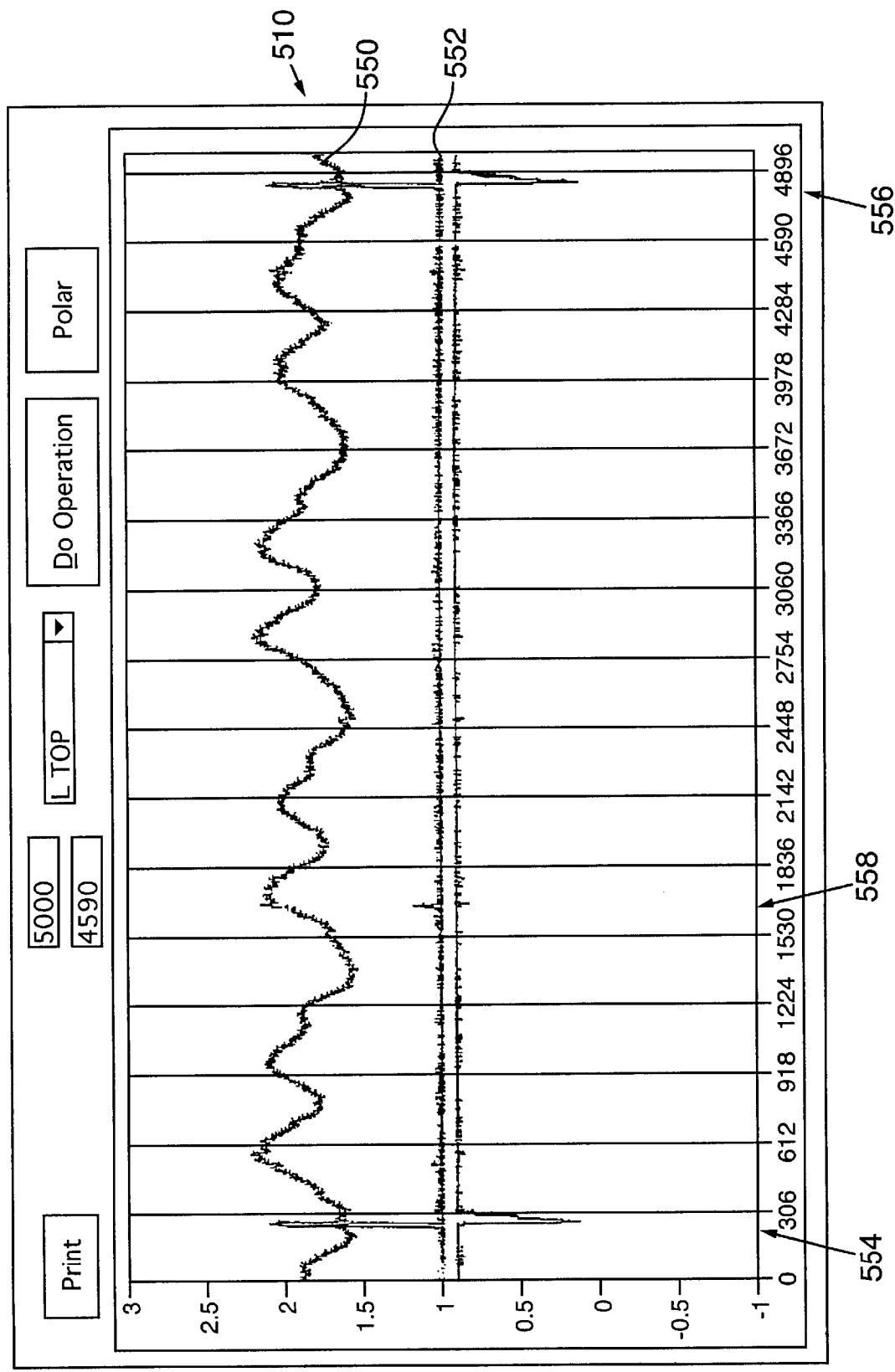
FIG. 17 illustrates a display of a detector output before and after processing to indicate defects.
Figures 18, 19:
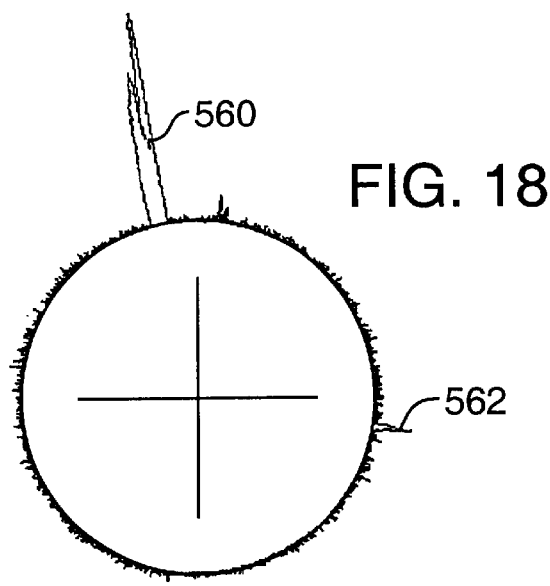
FIG. 18 is a display in polar form of processed signals from a detector.
FIG. 19 illustrates one form of a visual display indicating the results of testing of various wafers in a wafer cassette.
Figure 20:
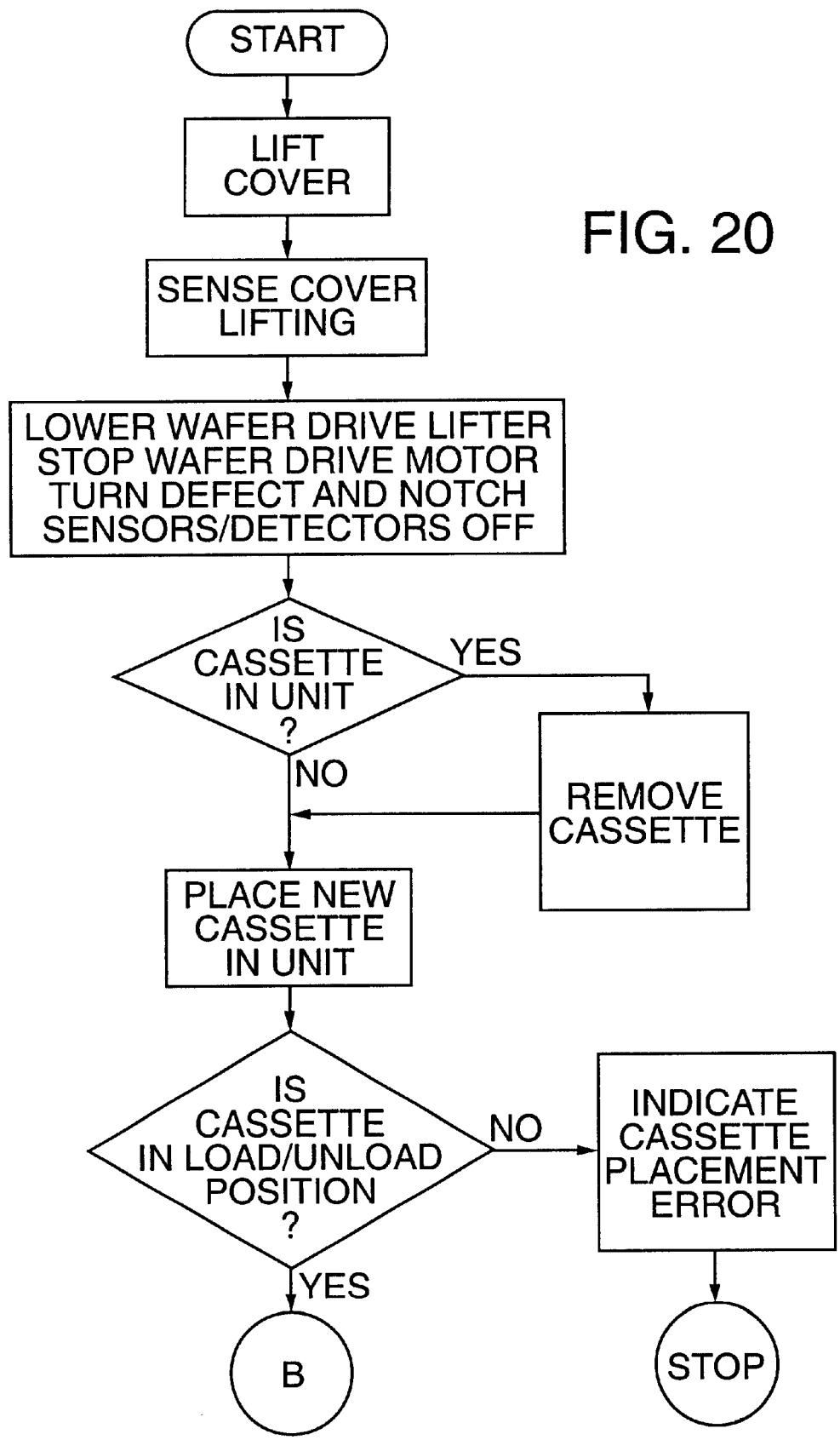
FIGS. 20–24 illustrate a flow chart of an exemplary wafer detecting process utilizing the apparatus of FIG. 1 and the circuit of FIG. 16.
Figure 21:
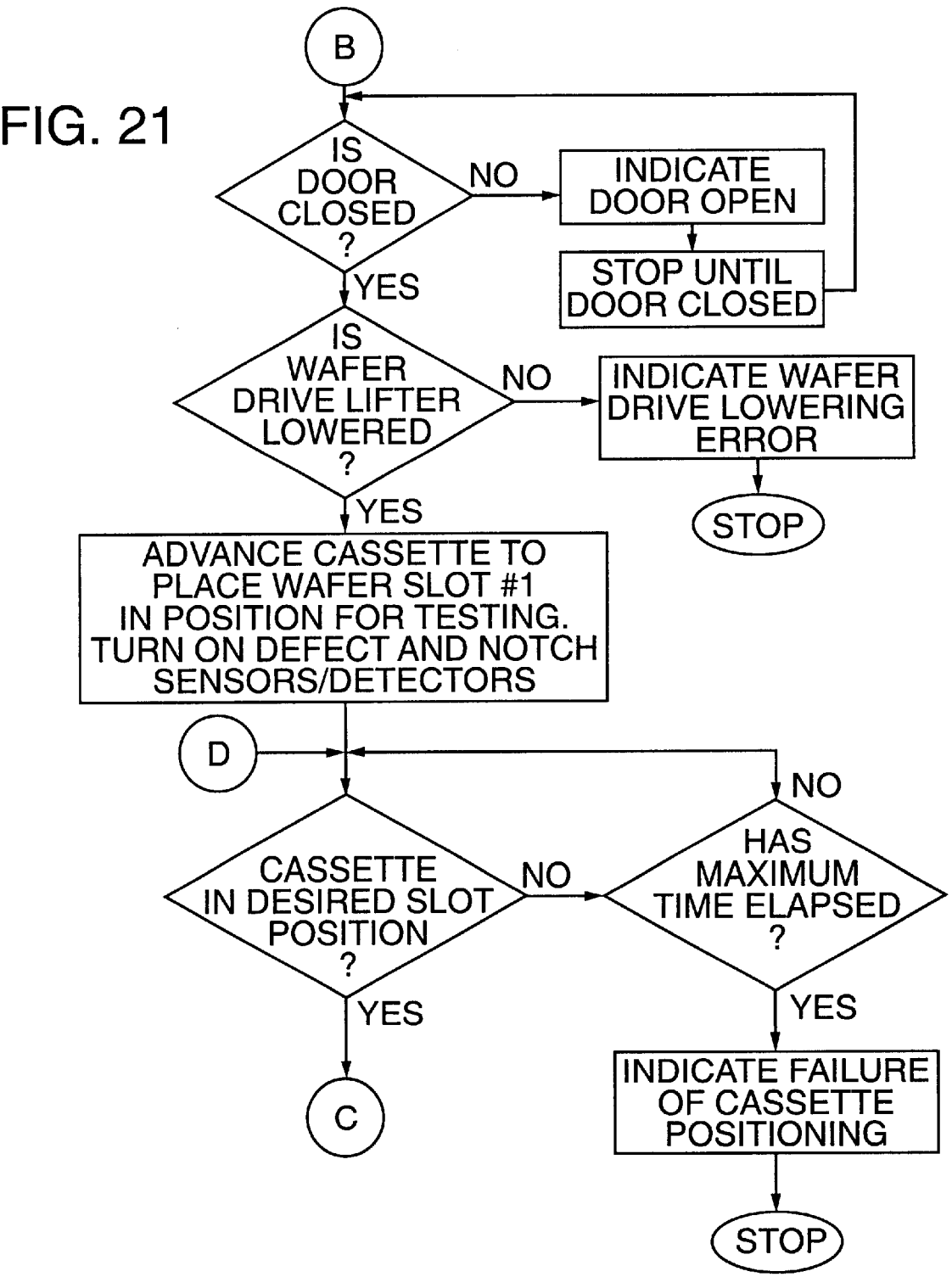
Figure 22:
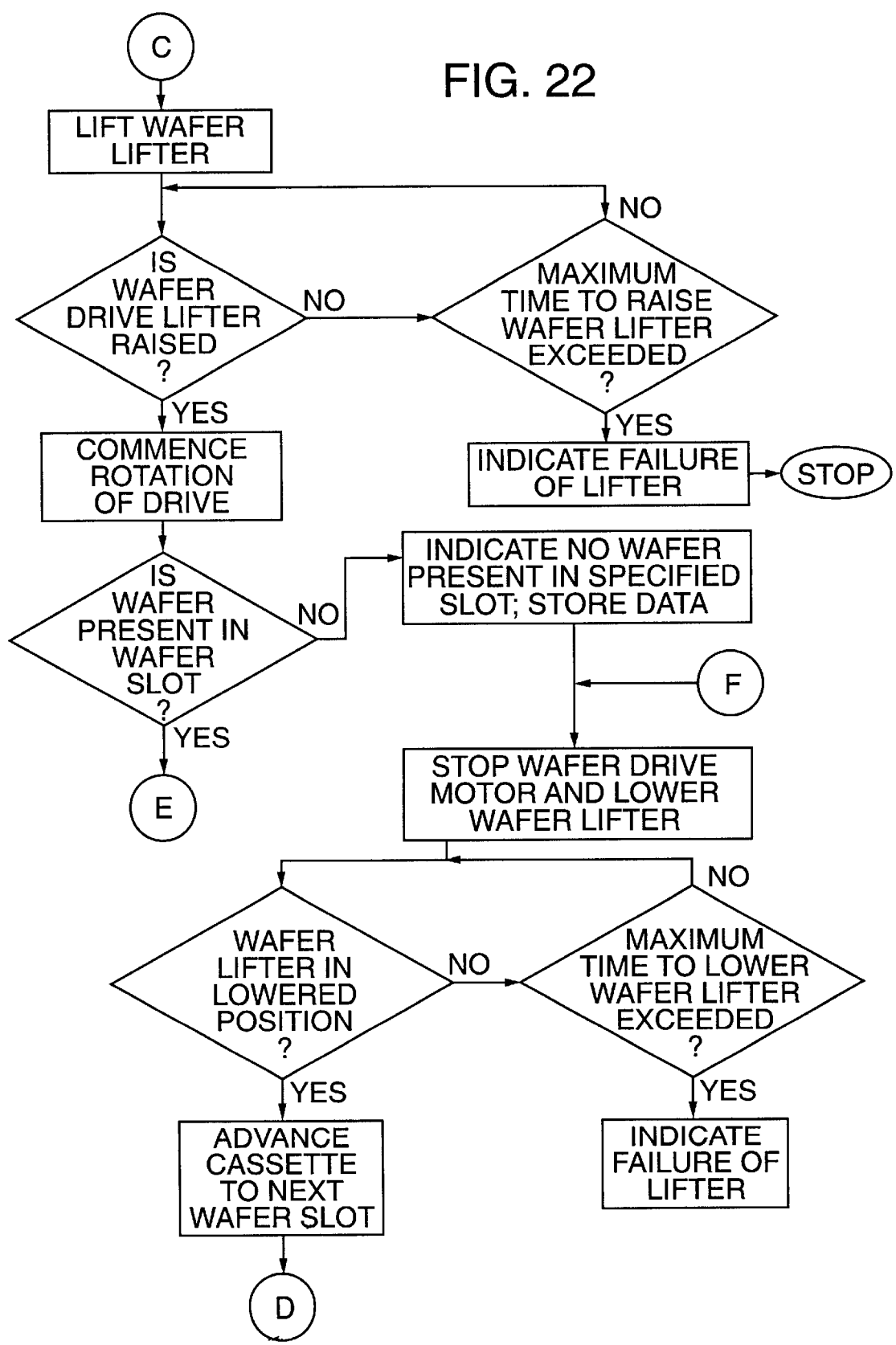
Figure 23:
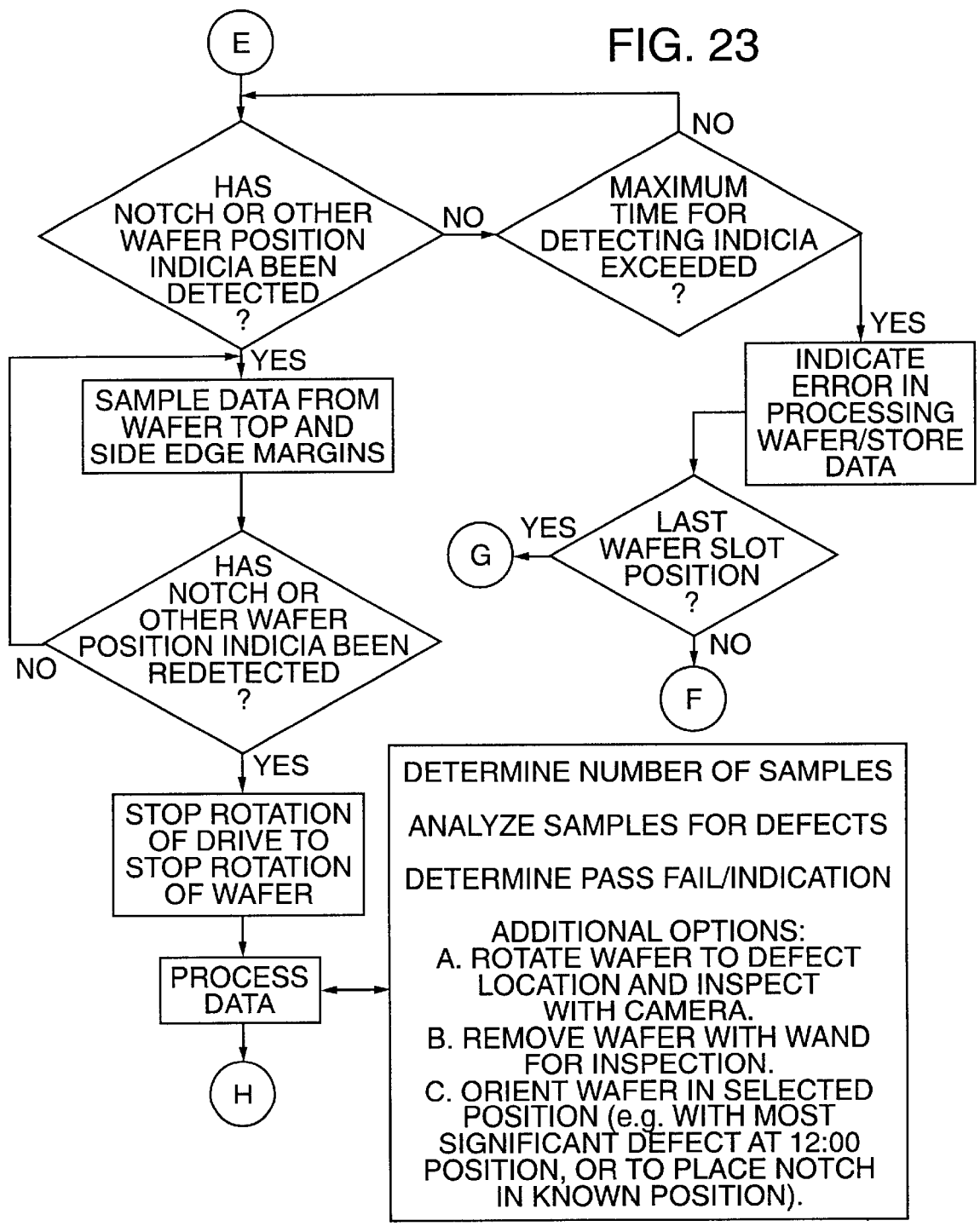
Figure 24:
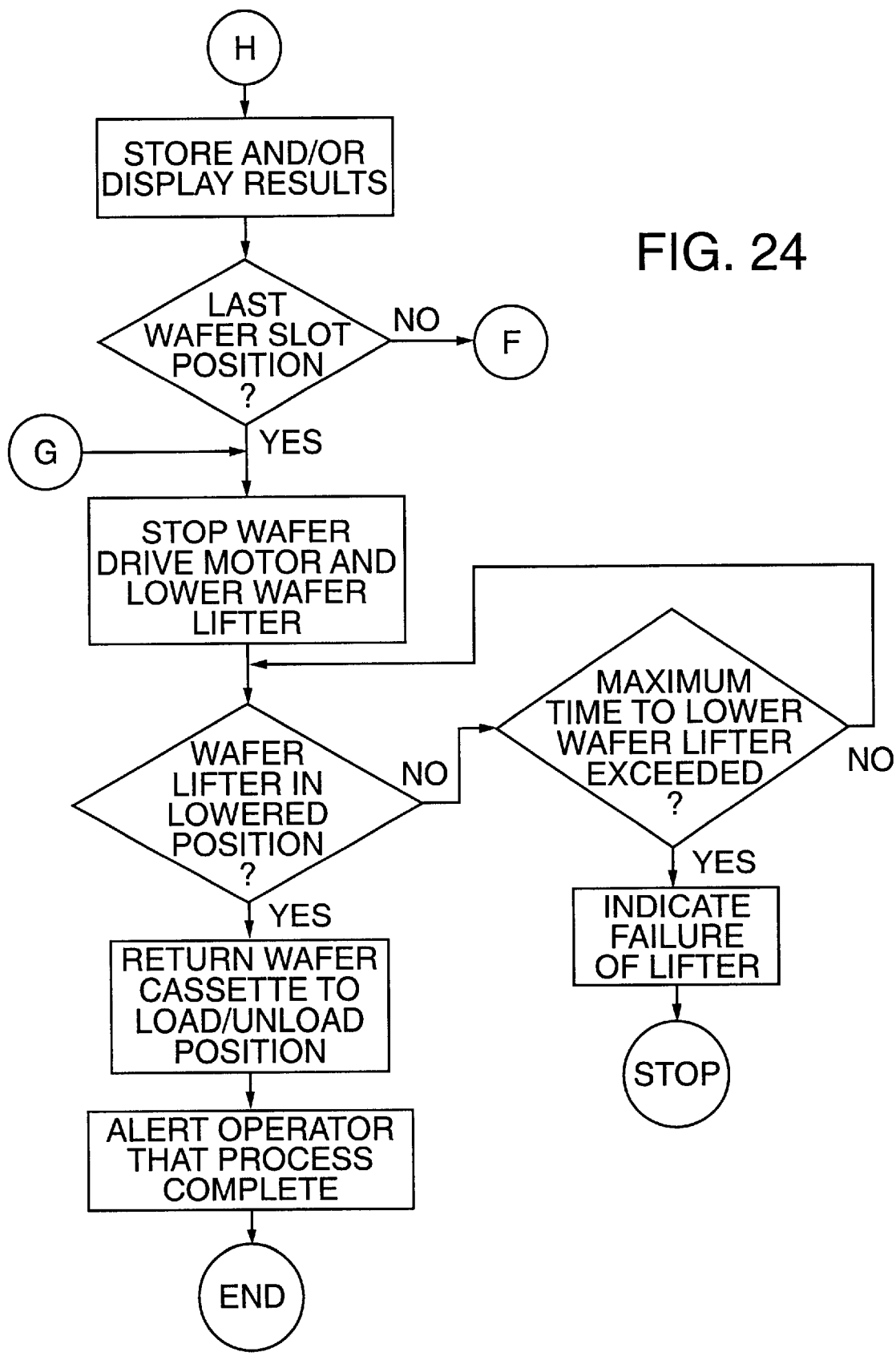

The results of the evaluation of a particular wafer may be stored for subsequent display or may be displayed as they are being generated. The display may take any of a number of forms. FIG. 17 shows a screen shot of a computer monitor 510 illustrating exemplary test results. The line labeled 550 is the output of one of the light detectors. The line indicated at 552 is the first derivative of the samples displayed on line 550. The first detection of the notch occurred generally at location 554 along the x-axis. The second detection of the notch occurred generally at 556. A defect in the wafer is indicated to have occurred at location 558 along the x-axis. Although less clear, this defect can be seen at the same location along wave form 550. Depending upon where the threshold is established, the defect at 558 will be indicated. Criteria may be established for determining whether particular wafers pass or fail depending for example on the number and magnitude of the differences that are found, which correspond to the number and significance of the defects. With reference to FIG. 18, for a given wafer the difference data can be plotted in polar graph form. This yields a circle with spikes indicating the location of the defects relative to the notch. In the graph of FIG. 18, the position of the notch is indicated at 560 and the position of a defect is indicated at 562. This display can be visually presented when, for example the operator designates a wafer that the operator wants to review for the existence of possible defects in the wafer. A threshold circle may also be included in FIG. 18 to help the operator determine whether a significant defect has been determined. The difference data from the various detectors corresponding to the wafer front edge margin, outer edge and rear edge margin sensors may be displayed together, in various combinations, or individually.

FIG. 19 discloses another optional form of display. In FIG. 19, a visual representation 564 of a cassette is shown. In this example, the cassette has 25 wafer positions (although cassettes of different sizes may be accommodated). For a given type of cassette, data is input into the computer to indicate the number of wafer slots and the positioning between the wafer slots so that the computer can control indexing of the cassette. In FIG. 19, again, the specific slots are numbered 1–25. In addition, visual indicators are provided to inform the operator of the condition of the various wafers in the slots. In the example depicted in FIG. 19, slots 6, 9 and 15 are shown blank. This corresponds to the system determining that no wafers were present in these slots of the cassette. The slots with a plus indicia indicate those wafers which have passed the edge defect testing procedure. The slots 5, 10 and 21 contain X's to indicate wafers that have failed the edge defect testing. Other visual indicia may be provided. For example, failed wafers may be marked in a particular color such as red, passed wafers in a particular color such as green and again missing wafers in an alternative color or shown as empty slots.

FIGS. 20–24 illustrate one suitable control sequence for the above described embodiments of a wafer edge defect sensor apparatus. This sequence is readily apparent from the flow chart.

In one suitable approach, upon powering up of the system, the computer confirms that the wafer drive assembly 70 is off and in a lowered position and also that the platform 20 is shifted to the unload/load position. In addition, one can exit the system at any time using an exit command with the computer then causing the shutting off the wafer drive motor, the lowering of the wafer drive and the return of the cassette to the load/unload position.

The procedure set forth in FIGS. 20–24 may be varied but again provides one specific approach which may be utilized. For example, the presence of a wafer in a slot may be detected in a number of ways. In the disclosed flow chart, a specific approach involves commencing the rotation of the drive 70. If a wafer notch detect sensor "off" signal is not determined within a particular time, for example within one fourth of a second of energizing the drive motor, then it is assumed that there is no wafer in this slot of the cassette. The system sequences to place the next wafer slot in a position for testing. In the event initial lifting of the cover is sensed, the wafer drive lifter is lowered, the wafer drive motor is stopped and the defect and notch sensor/detectors are turned off. Consequently, operators are not exposed to moving parts when the cover is lifted. Sensing of the presence of the cassette in the unit involves a determination of whether the cassette is in the unload/load position. Similarly, the cassette presence sensor provides an indication that the cassette has been properly placed in the apparatus. Processing of the wafers does not commence until the door is closed. In addition, the cassette is not indexed to place the first slot in position for evaluation of a wafer contained in the slot until the wafer drive lifter has been lowered to place it out of the way of the cassette. As the cassette is indexed to successive wafer slot positions (and under the computer control the user may specify that certain slot positions be skipped as the user may know that certain positions have no wafers), the system is monitored to determine if the cassette is at the desired position. When the cassette is at the desired position, the wafer lifter is raised and rotation of the wafer drive commences. If a wafer is present in the wafer slot, the system watches for the detection of the notch or other wafer position indicia. When this occurs, data is sampled until the wafer position indicia is re-detected. The rotation of the drive is then stopped and data is stored and/or processed. Eventually the last wafer slot position and a wafer (if any) contained therein is checked. The wafer drive motor is then stopped and the wafer lifter is lowered. The wafer cassette is then returned to the load/unload position and the operator is alerted that the process is complete.

In the above system, the computer may also be controlled to rotate a particular wafer to a given position as directed by an operator.

Figure 25:
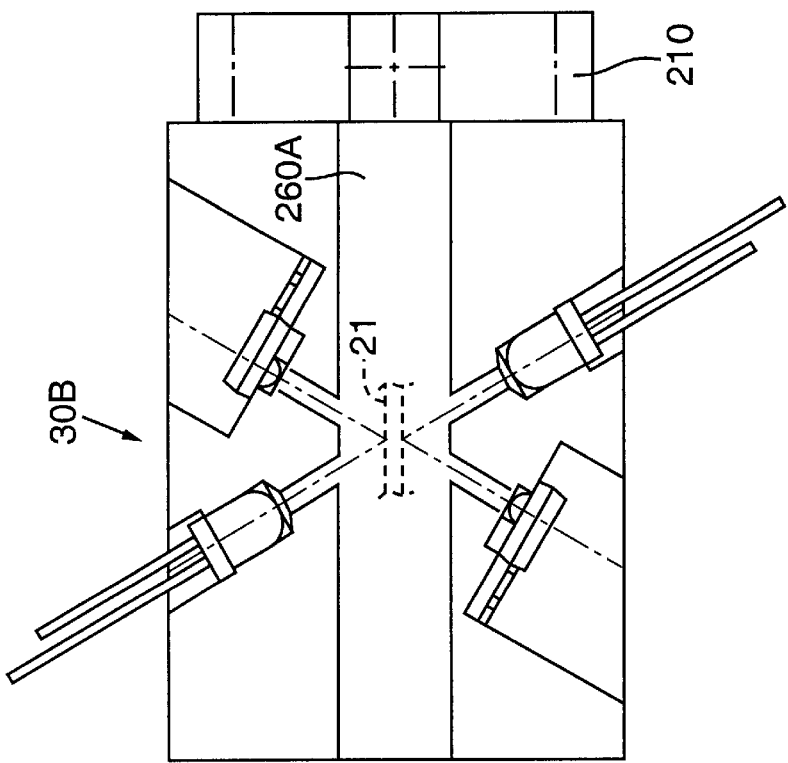
FIGS. 25 and 26 illustrate alternative arrangements of light sources and detectors utilized in an electronic media edge detect detection apparatus.
Figure 26:
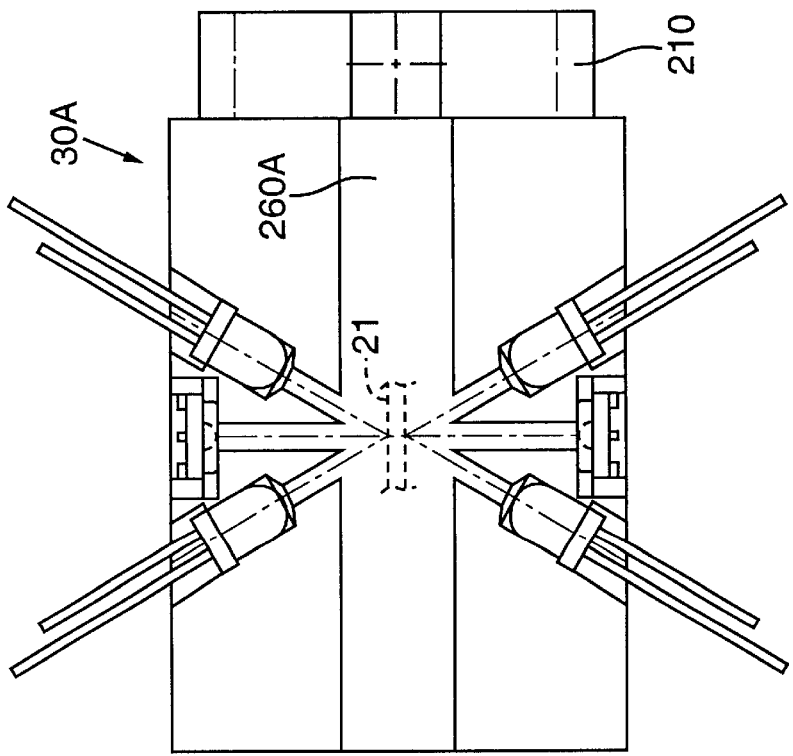
Figure 27:
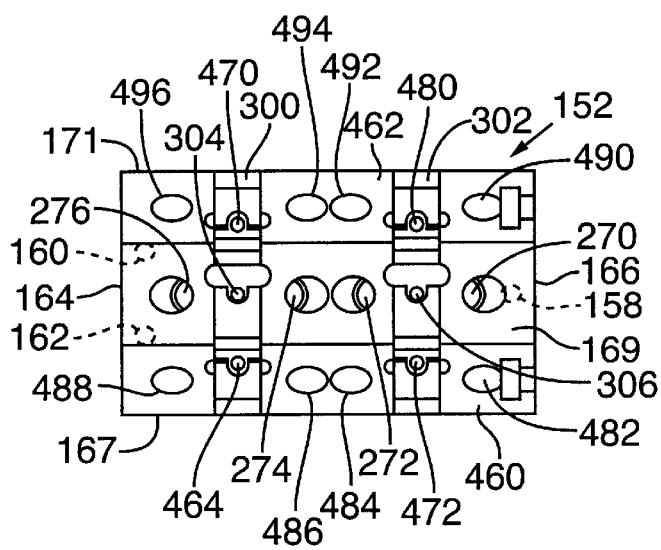
FIG. 27 illustrates a top view of another form a sensor and detector support for supporting a plurality of light sources and light detectors, such as LEDs and detectors of light from the LEDs.
Figure 29:
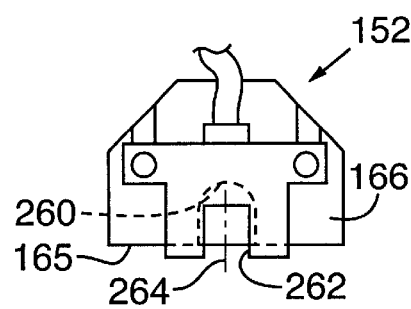
FIG. 29 is an end view of the support of FIG. 27 with a wafer edge indicia detector for detecting a notch or other indicia to indicate a reference position on the wafer.
Figure 28:
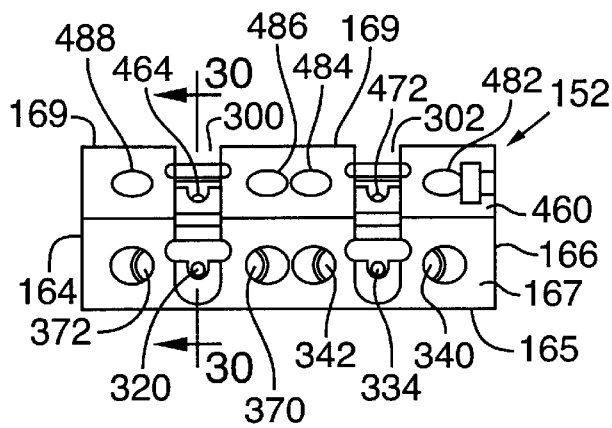
FIG. 28 is a side elevation view of the support of FIG. 27.

Numerous modifications may be made to the electronic media edge defect detection apparatus described above. We claim as our invention all such modifications. For example, multiple wafers may be simultaneously examined by the addition of additional idler arms, sensor assemblies and drive roll mechanisms to the apparatus. For example, in the case of a 25-position cassette, five such devices may be used and spaced apart to test five wafers at a time. FIG. 25 shows an alternative form of sensor assembly designated 30A utilizing two light emitters and a single detector focusing on one side edge margin of the wafer 21, two light emitters and a single detector focused on the opposite side edge margin of the wafer 21 and optionally (not shown) a third set of two light emitters and a single detector focused on the outer edge of the wafer 21. In this example monitoring of defects at the outer edge of the wafer may be eliminated (this approach may also be used in the previously described embodiments). In the form shown in FIG. 26, although less desirable, light from a single light emitter is reflected off a first side edge margin of the wafer 21 to a single detector; light from a second light emitter is reflected off of the opposite side edge of the wafer to a single detector; with a similar arrangement optionally being used to monitor the outer edge of the wafer. The amount of light that reaches the detectors in FIG. 26 is affected by the defects as defects tend to scatter the light away from being reflected to the detectors. The embodiment of FIG. 26 is less desirable. In addition, the embodiment of FIG. 25 eliminates the redundancy provided by multiple emitters and detectors along each of the edge margins of a wafer and the benefits from such redundancy as previously described. Nevertheless, variations such as these illustrate the fact that the present invention is not limited to the specifically described embodiments.

We claim:

1. A method of determining the presence of defects along the edge of electronic media, the electronic media having first and second opposed side edge margins and an outer edge margin extending between the first and second side edge margins, the method comprising:

delivering light from at least one first light source to a first portion of the first side edge margin of the media;

delivering light from at least one second light source to a first portion of the second side edge margin of the media;

delivering light from at least one third light source to a first portion of the outer edge margin of the media;

positioning at least one first detector to detect a portion of the light delivered to the first portion of the first side edge margin that has been deflected by the first portion of the first side edge margin toward the at least one first detector, the at least one first detector providing a first output corresponding to the detected light which is detected by the at least one first detector;

positioning at least one second detector to detect a portion of the light delivered to the first portion of the second side edge margin that has been deflected by the first portion of the second side edge margin toward the at least one second detector, the at least one second detector providing a second output corresponding to the detected light which is detected by the at least one second detector;

positioning at least one third detector to detect a portion of the light delivered to the first portion of the outer edge margin that has been deflected by the first portion of the outer edge margin toward the at least one third detector, the at least one third detector providing a third output corresponding to the detected light which is detected by the at least one third detector;

moving the electronic media relative to the at least one first light source, the at least one first detector, the at least one second source, the at least one second detector; the at least one third light source and the at least one third detector;

processing the respective detector outputs to determine the presence of defects at the first and second side edge margins and outer edge of the electronic media; and indicating the presence of such defects.

2. A method according to claim 1 wherein there are at least two of said first light sources; at least two of said second light sources and at least two of said third light sources.

3. A method according to claim 1 including the act of adjusting the intensity of light from the respective at least one first, second and third light sources.

4. A method according to claim 3 comprising the act of automatically and independently adjusting the intensity of light from the at least one respective first, second and third light sources.

5. A method according to claim 1 further comprising:

delivering light from at least one fourth light source to a second portion of the first side edge margin of the media, the second portion being spaced in a first direction from the first portion of the first side edge margin of the media;

delivering light from at least one fifth light source to a second portion of the second side edge margin of the media, the second portion being spaced in the first direction from the first portion of the second side edge margin of the media;

delivering light from at least one sixth light source to a second portion of the outer edge margin of the media, the second portion being spaced in the first direction from the first portion of the outer edge margin of the media;

positioning at least one fourth detector to detect a portion of the light delivered to the second portion of the first side edge margin that has been deflected by the second portion of the first side edge margin toward the at least one fourth detector, the at least one fourth detector providing a fourth output corresponding to the detected light which is detected by the at least one fourth detector;

positioning at least one fifth detector to detect a portion of the light delivered to the second portion of the second side edge margin that has been deflected by the second portion of the second side edge margin toward the at least one fifth detector, the at least one fifth detector providing a fifth output corresponding to the detected light which is detected by the at least one fifth detector;

positioning at least one sixth detector to detect a portion of the light delivered to the second portion of the outer edge margin that has been deflected by the second portion of the outer edge margin toward the at least one sixth detector, the at least one sixth detector providing a sixth output corresponding to the detected light which is detected by the at least one sixth detector; and wherein the act of moving the electronic media comprises moving the electronic media relative to the at least one fourth light source, the at least one fourth detector, the at least one fifth light source, the at least one fifth detector, the at least one sixth light source and the at least one sixth detector.

6. A method according to claim 5 wherein there are at least two of said first, second, third, fourth, fifth and sixth light sources.

7. A method according to claim 1 wherein the acts of delivering light from the respective light sources comprise the acts of delivering light from light sources which comprise LEDs.

8. A method according to claim 1 further comprising the acts of:

delivering light from at least one seventh light source to a third portion of the first side edge margin of the media, the third portion of the first side edge margin being positioned closer to the first portion of the outer edge margin of the media than the first portion of the first side edge margin;

delivering light from at least one eighth light source to a third portion of the second side edge margin of the media, the third portion of the second side edge margin of the media being closer to the first portion of the outer edge margin than the first portion of the second side edge margin of the media;

positioning at least one seventh detector to detect a portion of the light delivered to the third portion of the first side edge margin that has been deflected by the third portion of the first side edge margin toward the at least one seventh detector, the at least one seventh detector providing a seventh output corresponding to the detected light which is detected by the at least one seventh detector;

positioning at least one eighth detector to detect a portion of the light delivered to the third portion of the second side edge margin that has been deflected by the third portion of the second side edge margin toward the at least one eighth detector, the at least one eighth detector providing an eighth output corresponding to the detected light which is detected by the at least one eighth detector; and wherein the act of moving the electronic media further comprises the act of moving the electronic media relative to the at least one seventh light source, the at least one seventh detector, the at least one eighth light source and the at least one eighth detector.

9. A method according to claim 8 wherein there are at least two of the seventh and eighth light sources.

10. A method according to claim 8 further comprising:

delivering light from at least one ninth light source to a fourth portion of the first side edge margin of the media, the fourth portion being positioned closer to the second second portion of the outer edge margin than the portion of the first side edge margin of the media;

delivering light from at least one tenth light source to a fourth portion of the second side edge margin of the media, the fourth portion of the second side edge margin of the media being closer to the second portion of the outer edge margin than the second portion of the second side edge margin of the media;

positioning at least one ninth detector to detect a portion of the light delivered to the fourth portion of the first side edge margin that has been deflected by the fourth portion of the first side edge margin toward the at least one ninth detector, the at least one ninth detector providing a ninth output corresponding to the detected light which is detected by the at least one ninth detector;

positioning at least one tenth detector to detect a portion of the light delivered to the fourth portion of the second side edge margin that has been deflected by the fourth portion of the second side edge margin toward the at least one tenth detector, the at least one tenth detector providing a tenth output corresponding to the detected light which is detected by the at least one tenth detector; and wherein the act of moving the electronic media comprises the act of moving the electronic media relative to the at least one ninth light source, the at least one ninth detector, the at least one tenth light source and the at least one tenth detector.

11. A method according to claim 10 wherein there are at least two of said ninth light sources and at least two of said tenth light sources.

12. A method according to claim 1 further comprising the acts of:

lifting the electronic media and wherein the act of moving the electronic media comprises the act of moving the lifted electronic media at least during a portion of the time the electronic media is lifted, and further comprising the act of lowering the electronic media.

13. A method according to claim 1 wherein the act of processing the detected light comprises the act of determining the first derivative of changes in the respective detector outputs and comparing the first derivative of such changes to a threshold.

14. A method according to claim 1 comprising the act of tracking the position of the media as it is moved and correlating the position of the media with the detected defects such that the location of the defects is determined and wherein the indicating act comprises the act of indicating the presence of such defects.

15. A method according to claim 1 wherein the media includes a position indicator and wherein the method of processing the detect or outputs comprises the act of ignoring light detected at least at the location of the position indicator.

16. A method according to claim 15 wherein the act of ignoring comprises the act of ignoring light detected from locations at either side of the position indicator and at the location of the position indicator.

17. A method according to claim 1 wherein the act of moving the electronic media comprises the act of turning a disk.

18. A method according to claim 1 wherein the act of indicating the presence of defects comprises the act of indicating those disks in a cassette of disks which contain an unacceptable level of defects.

19. A method of determining the presence of defects along the edge of electronic media, the electronic media having first and second opposed side edge margins and an outer edge margin extending between the first and second side edge margins, the method comprising:

moving the media;

directing light from plural light sources toward the first side edge margin of the media at least during a portion of the time that the media is moving;

directing light from plural light sources toward the second side edge margin of the media at least during a portion of the time that the media is moving, the light being directed from plural light sources toward the second side edge margin of the media simultaneously with the light being directed from plural light sources toward the first side edge margin of the media;

detecting light scattered from the media toward plural detectors; and determining the presence of defects from the detected light.

20. A method of determining the presence of defects along the edge of electronic media, the electronic media having first and second opposed side edge margins and an outer edge margin extending between the first and second side edge margins, the method comprising:

moving the media;

directing light from plural light sources toward the first side edge margin of the media at least during a portion of the time that the media is moving;

directing light from plural light sources toward the second side edge margin of the media at least during a portion of the time that the media is moving;

further comprising the act of directing light from plural light sources toward the outer edge margin of the media during at least a portion of the time that the media is moving;

detecting light scattered from the media toward plural detectors; and determining the presence of defects from the detected light.

21. A method according to claim 20 in which the acts of directing light comprises directing light through respective elongated light directing bores and the act of detecting light comprises the act of detecting light passing through respective elongated light detecting bores.

22. A method of determining the presence of defects along the edge of electronic media, the electronic media having first and second opposed side edge margins and an outer edge margin extending between the first and second side edge margins, the method comprising:

moving the media;

directing light from plural light sources toward the first side edge margin of the media at least during a portion of the time that the media is moving;

directing light from plural light sources toward the second side edge margin of the media at least during a portion of the time that the media is moving and receiving light directed from the light sources directed toward the first side edge margin of the media and without interrupting the movement of the media between the act of directing light from plural light sources toward the first side edge margin of the media and the act of directing light from plural light sources toward the second side edge margin of the media;

detecting light scattered from the media toward plural detectors; and determining the presence of defects from the detected light.

23. A method of determining the presence of defects along the edge of electronic media, the electronic media having first and second opposed side edge margins and an outer edge margin extending between the first and second side edge margins, the method comprising:

moving the media;

directing light from a first set of plural light sources toward the first side edge margin of the media at least during a portion of the time that the media is moving;

directing light from a second set of plural light sources toward the second side edge margin of the media at least during a portion of the time that the media is moving and receiving light directed from the first set of plural light sources and without inverting the media to position the second side edge margin to receive light from the second set of plural light sources;

detecting light scattered from the media toward plural detectors; and determining the presence of defects from the detected light.

* * * * *